(12) United States Patent
Pikov et al.

(10) Patent No.: US 12,017,073 B2
(45) Date of Patent: Jun. 25, 2024

(54) DEVICES, SYSTEMS, AND METHODS FOR DELIVERING THERAPY TO A SACRAL NERVE

(71) Applicant: EnteroMed Ltd, Kowloon (HK)

(72) Inventors: Victor Eugene Pikov, Pasadena, CA (US); Jianfeng Chen, Tulsa, OK (US); Min Ni, Nanjing (CN)

(73) Assignee: Enteromed Ltd, Hong Kong (HK)

( * ) Notice: Subject to any disclaimer, the term of this patent is extended or adjusted under 35 U.S.C. 154(b) by 927 days.

(21) Appl. No.: 16/874,522

(22) Filed: May 14, 2020

(65) Prior Publication Data

US 2020/0360696 A1 Nov. 19, 2020

Related U.S. Application Data

(60) Provisional application No. 62/848,976, filed on May 16, 2019.

(51) Int. Cl.
*A61N 1/36* (2006.01)

(52) U.S. Cl.
CPC ....... *A61N 1/36139* (2013.01); *A61N 1/3606* (2013.01)

(58) Field of Classification Search
CPC .......................... A61N 1/36139; A61N 1/3606
(Continued)

(56) References Cited

U.S. PATENT DOCUMENTS 6,091,992 A 7/2000 Bourgeois et al.
6,243,607 B1 6/2001 Mintchev et al.
(Continued)

FOREIGN PATENT DOCUMENTS

CN 101060884 A 10/2007
CN 105498085 A 4/2016
(Continued)

OTHER PUBLICATIONS

International Search Report dated May 29, 2020, for PCT Application No. PCT/CN2020/077799, filed on Mar. 4, 2020, 5 pages.
(Continued)

*Primary Examiner* — Erin M Piateski
(74) *Attorney, Agent, or Firm* — Cooley LLP

(57) ABSTRACT

Systems for delivering therapy to a nerve in a patient may comprise a plurality of sensors, such as a cardiac sensor, a disease activity sensor, and a bodily activity sensor, an implantable pulse generator, and an implantable signal delivery device. The implantable signal delivery device may be configured to deliver a stimulation signal to the nerve. The implantable pulse generator may comprise a microcontroller configured to calculate a heart rate parameter from cardiac data received from the cardiac sensor, calculate a disease activity parameter from disease activity data received from the disease activity sensor, calculate a bodily activity parameter from bodily activity data received from a bodily activity sensor, determine an autonomic nervous system state, physiological state, and/or disease state of the patient based on the heart rate parameter, the disease activity parameter, and the bodily activity parameter, and adjust a nerve stimulation parameter of a stimulation signal based on the determined autonomic nervous system state, the physiological state, and/or the disease state.

31 Claims, 14 Drawing Sheets

(58) Field of Classification Search
USPC .......................................................... 607/62
See application file for complete search history.

(56) References Cited

U.S. PATENT DOCUMENTS

| | | | |
|---|---|---|---|
| 6,449,511 | B1 | 9/2002 | Mintchev et al. |
| 6,735,474 | B1 | 5/2004 | Loeb et al. |
| 6,826,428 | B1 | 11/2004 | Chen et al. |
| 6,853,862 | B1 | 2/2005 | Marchal |
| 7,664,551 | B2 | 2/2010 | Cigaina |
| 7,778,711 | B2 | 8/2010 | Ben-David et al. |
| 7,925,351 | B2 | 4/2011 | Khawaled et al. |
| 8,095,218 | B2 | 1/2012 | Gross et al. |
| 8,285,373 | B2 | 10/2012 | Ternes et al. |
| 8,355,797 | B2 | 1/2013 | Caparso et al. |
| 8,406,877 | B2 | 3/2013 | Smith et al. |
| 8,594,811 | B2 | 11/2013 | Chen et al. |
| 8,600,521 | B2 | 12/2013 | Armstrong et al. |
| 8,666,495 | B2 | 3/2014 | Harel et al. |
| 10,922,133 | B2 | 2/2021 | He et al. |
| 2003/0055463 | A1 | 3/2003 | Gordon et al. |
| 2005/0015117 | A1 | 1/2005 | Gerber |
| 2005/0055063 | A1 | 3/2005 | Loeb et al. |
| 2005/0060005 | A1 | 3/2005 | Boggs, II et al. |
| 2005/0143783 | A1 | 6/2005 | Boveja et al. |
| 2005/0209653 | A1 | 9/2005 | Herbert et al. |
| 2006/0235477 | A1 | 10/2006 | Rom |
| 2007/0016262 | A1 | 1/2007 | Gross et al. |
| 2009/0036945 | A1 | 2/2009 | Chancellor et al. |
| 2009/0138061 | A1 | 5/2009 | Stephens et al. |
| 2009/0240194 | A1 | 9/2009 | Keimel et al. |
| 2010/0211135 | A1 | 8/2010 | Caparso et al. |
| 2011/0295335 | A1 | 12/2011 | Sharma et al. |
| 2012/0130444 | A1 | 5/2012 | Wei et al. |
| 2012/0197338 | A1 | 8/2012 | Su et al. |
| 2012/0259382 | A1 | 10/2012 | Trier et al. |
| 2012/0316451 | A1 | 12/2012 | Province et al. |
| 2013/0150940 | A1 | 6/2013 | Wilson et al. |
| 2013/0158618 | A1 | 6/2013 | Libbus et al. |
| 2013/0238047 | A1 | 9/2013 | Libbus et al. |
| 2013/0241745 | A1 | 9/2013 | Colvin, Jr. et al. |
| 2013/0289647 | A1 | 10/2013 | Bhadra et al. |
| 2014/0046398 | A1 | 2/2014 | Sachs et al. |
| 2014/0249595 | A1 | 9/2014 | Chancellor et al. |
| 2014/0253038 | A1 | 9/2014 | Posa |
| 2014/0277250 | A1 | 9/2014 | Su et al. |
| 2015/0134027 | A1 | 5/2015 | Kaula et al. |
| 2015/0142082 | A1 | 5/2015 | Simon et al. |
| 2015/0196351 | A1 | 7/2015 | Stone et al. |
| 2016/0303376 | A1 | 10/2016 | Dinsmoor et al. |
| 2016/0367814 | A1 | 12/2016 | Pless et al. |
| 2017/0120055 | A1* | 5/2017 | Rezai .................. A61N 1/0551 |
| 2017/0143972 | A1 | 5/2017 | Hershey et al. |
| 2017/0203103 | A1* | 7/2017 | Levine ................. A61B 5/7257 |
| 2017/0203110 | A1 | 7/2017 | Imran |
| 2018/0193643 | A1* | 7/2018 | Chen .................. A61N 1/36053 |
| 2019/0060647 | A1 | 2/2019 | Su et al. |
| 2020/0188671 | A1* | 6/2020 | Lovett ................. A61B 5/4836 |
| 2021/0393954 | A1 | 12/2021 | Pikov |

FOREIGN PATENT DOCUMENTS

| | | |
|---|---|---|
| CN | 105521561 A | 4/2016 |
| CN | 106345056 A | 1/2017 |
| CN | 107789733 A | 3/2018 |
| CN | 108463163 A | 8/2018 |
| CN | 207734348 U | 8/2018 |
| GB | 1 577 682 A | 10/1980 |
| JP | 2002-102360 A | 4/2002 |
| JP | 2006-508768 A | 3/2006 |
| WO | WO-2004/000416 A1 | 12/2003 |
| WO | WO-2010/067360 A2 | 6/2010 |
| WO | WO-2010/067360 A3 | 6/2010 |
| WO | WO-2016/137926 A1 | 9/2016 |
| WO | WO-2017/002104 A1 | 1/2017 |
| WO | WO-2018/053336 A1 | 3/2018 |
| WO | WO-2018/152064 A1 | 8/2018 |

OTHER PUBLICATIONS

International Search Report dated Aug. 18, 2020, for PCT Application No. PCT/CN2020/090615, filed on May 15, 2020, 3 pages.

Written Opinion of the International Searching Authority dated May 29, 2020, for PCT Application No. PCT/CN2020/077799, filed on Mar. 4, 2020, 5 pages.

Written Opinion of the International Searching Authority dated Aug. 18, 2020, for PCT Application No. PCT/CN2020/090615, filed on May 15, 2020, 4 pages.

Cheng, J. et al. (2020). "Potential of electrical neuromodulation for inflammatory bowel disease," Inflamm Bowel Dis. 26:1119-1130.

De las Casas, S.G. et al. (2019). "Sacral nerve stimulation for constipation: long-term outcomes," Techniques in coloproctology 23:559-564.

Guo, J. et al. (2019). "Sacral nerve stimulation improves colonic inflammation mediated by autonomic-inflammatory cytokine mechanism in rats," Neurogastroenterol Motil. 31:e13676.

Huang, Z. et al. (2019). "Sacral nerve stimulation with appropriate parameters improves constipation in rats by enhancing colon motility mediated via the autonomic-cholinergic mechanisms," Am J Physiol Gastrointest Liver Physiol. 317:G609-G617.

Jin, H. et al. (2017). "Anti-inflammatory effects and mechanisms of vagal nerve stimulation combined with electroacupuncture in a rodent model of TNBS-induced colitis," Am J Physiol Gastrointest Liver Physiol. 313:G192-G202.

Li, S. et al. (2017). "Pulse Width-Dependent Effects of Intestinal Electrical Stimulation for Obesity: Role of Gastrointestinal Motility and Hormones," Obes. Surg. 27:70-77.

Liu, J. et al. (2011). "Hypoglycemic Effects of Intraluminal Intestinal Electrical Stimulation in Healthy Volunteers," Obes. Surg. 21:224-230.

Ni, M. et al. (2019). "Anti-Inflammatory Effects and Mechanisms of Sacral Nerve Stimulation Performed via Acupuncture Needles on Ulcerative Colitis," Gastroenterology 156:S-585.

Pasricha, T.S. et al. (2020). "Sacral nerve stimulation prompts vagally-mediated amelioration of rodent colitis," Physiol Rep. 8:e14294, 7 total pages.

Tu, L. et al. (2020). "Anti-inflammatory effects of sacral nerve stimulation: a novel spinal afferent and vagal efferent pathway," Am J Physiol Gastrointest Liver Physiol. 318:G624-G634.

Tu, L. (2020). "Sacral nerve stimulation ameliorates colonic barrier functions in a rodent model of colitis," Neurogastroenterology & Motility, p. e13916, 49 total pages.

Yin, J. et al. (2007). "Potential of Intestinal Electrical Stimulation for Obesity: A Preliminary Canine Study," Obesity 15:1133-1138.

Zhang, N. et al. (2020). "A novel method of sacral nerve stimulation for colonic inflammation," Neurogastroenterol Motil., p. e13825, 13 total pages.

Non-Final Office Action mailed on Mar. 26, 2024, for U.S. Appl. No. 17/466,933, filed Sep. 3, 2021, 7 pages.

* cited by examiner

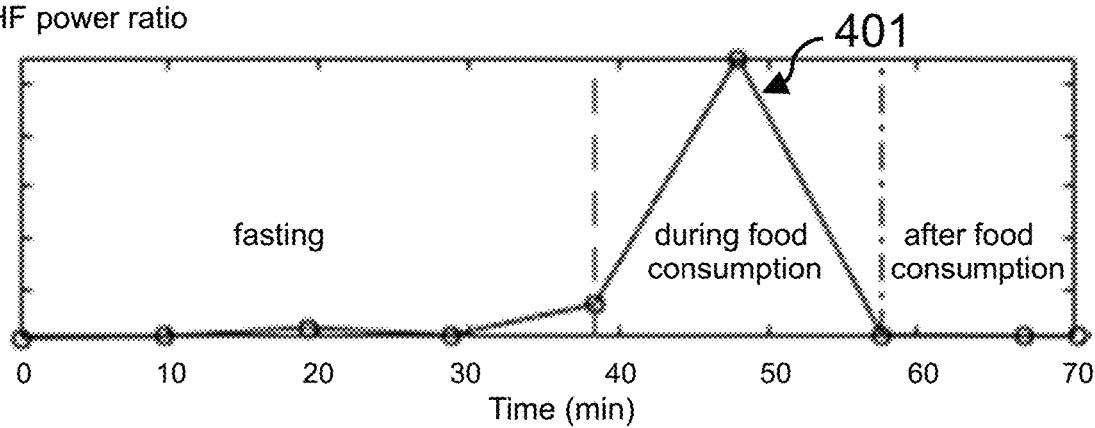
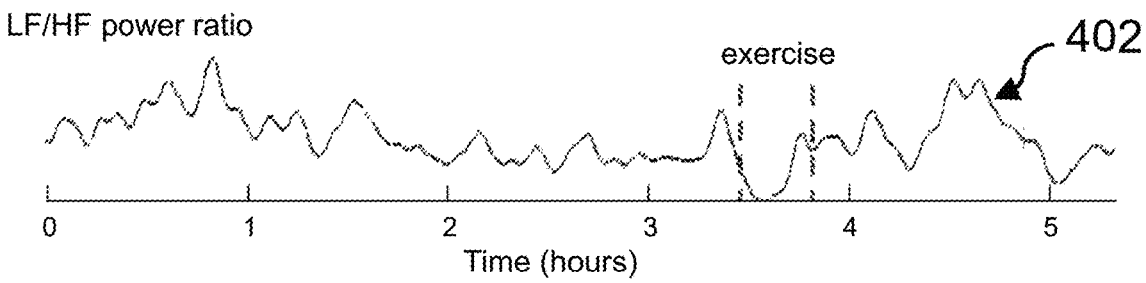
Fig. 7

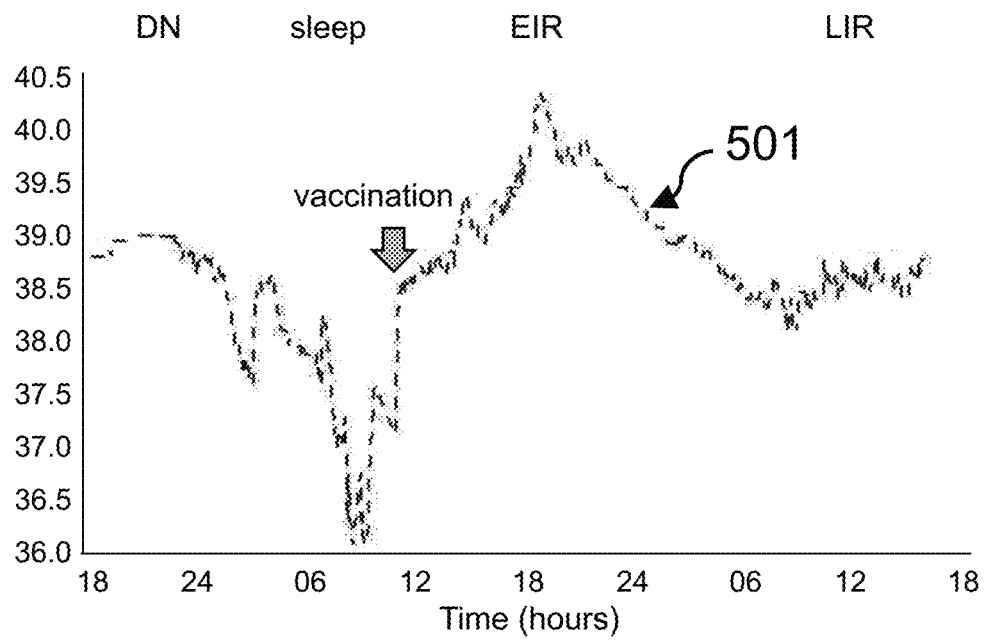
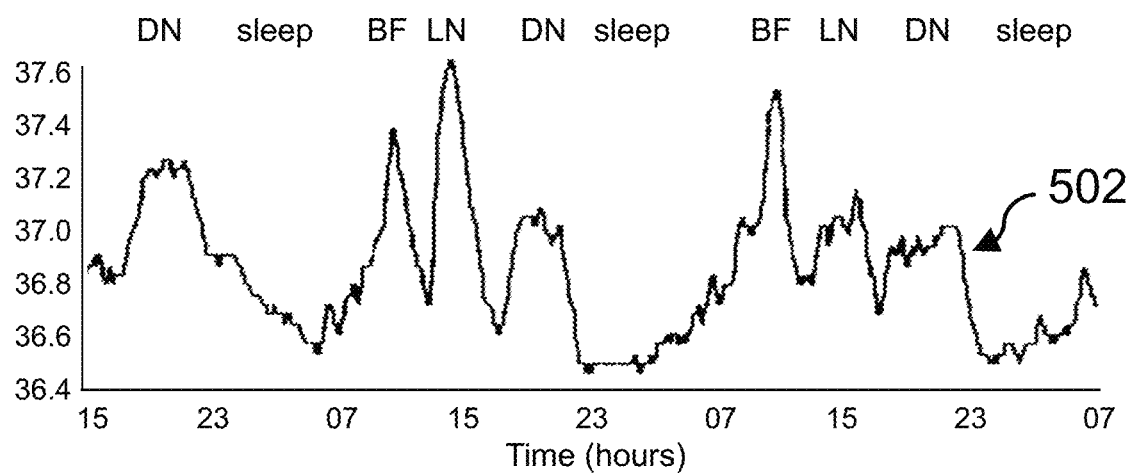
Fig. 8

| Patient-provided autonomic nervous system state, physiological state, and disease state | LF power | HF power | LF/HF ratio | IDA amp. | MA amp. | CR sleep |
|---|---|---|---|---|---|---|
| sympathetic activation | high | low | high | low | low | low |
| flare | medium | low | high | high | medium | low |
| physical exercise | low | high | low | low | high | low |
| during light meal | medium | medium | medium | low | medium | low |
| during heavy meal | high | low | high | low | high | low |
| after heavy meal | medium | medium | medium | low | medium | low |
| deep sleep | medium | high | low | low | low | high |
| REM sleep | high | low | high | low | low | medium |

701 — Patient-provided autonomic nervous system state, physiological state, and disease state 702 — Input layer nodes 703 — Hidden layer nodes 704 — Output layer node Physiological or disease state determined by algorithm

Fig. 10

DEVICES, SYSTEMS, AND METHODS FOR DELIVERING THERAPY TO A SACRAL NERVE

CROSS-REFERENCE TO RELATED APPLICATIONS

This application claims priority to U.S. Provisional Application Ser. No. 62/848,976, filed on May 16, 2019, the content of which is hereby incorporated by reference in its entirety.

TECHNICAL FIELD

This invention relates generally to the field of nerve stimulation, and more particularly, to new and useful devices, systems, and methods for non-surgical screening of patients, delivering electrical stimulation to a nerve, and/or adjusting delivery of electrical stimulation using autonomic nervous system parameters, disease activity parameters, and/or bodily activity parameters.

BACKGROUND

The increase in prevalence of chronic gastrointestinal disorders (such as irritable bowel syndrome, inflammatory bowel disease, ulcerative colitis, ulcerative proctitis, Crohn's disease, chronic constipation, chronic fecal incontinence, functional abdominal pain, gastroesophageal reflux disease, esophageal dysmotility, pseudo-obstruction, functional dyspepsia, gastroparesis, intestinal dysmotility, celiac disease, anorexia, colonic inertia, pancreatitis), chronic auto-immune diseases (such as autoimmune thyroid disease, ankylosing spondylitis, multiple sclerosis, myasthenia gravis, psoriasis, rheumatoid arthritis, Sjögren's syndrome, systemic lupus erythematosus, systemic sclerosis, juvenile idiopathic arthritis, Still's disease, macrophage activation syndrome, cytokine release syndrome, cytokine storm syndrome, hyperinflammation, acute respiratory distress syndrome, hemophagocytic lymphohistiocytosis, pneumonitis, chronic obstructive pulmonary disease, asthma, myocarditis), and metabolic disorders (such as type 2 diabetes mellitus, obesity, dyslipidemia, cardiometabolic disease, non-alcoholic fatty liver disease, chronic kidney disease, polycystic ovary syndrome, hypertension) constitutes a severe unmet medical need.

Conventional treatment of these disorders may include delivery of electrical stimulation to a particular anatomical structure, for example, a peripheral nerve. The stimulation may be delivered using stimulation delivery devices that are either inserted temporarily or chronically implanted. A clinician and/or patient may need to set and periodically adjust the stimulation parameters over time due to progression of the disease, therapy efficacy, and day-to-day variability in the disease manifestations. Generally, there are several stimulation parameters that are initially set up by the clinician with the patient's feedback. For the implanted devices, the initial setup typically occurs soon after the implantation. The clinician or patient then uses an external programmer to adjust these parameters when the patient's disease manifestations have changed. These adjustments may require office visits by the patient. In addition, because the stimulation often does not have to be applied continuously, patients are typically required to start and stop the stimulation based on disease manifestations, which can become onerous. Accordingly, there is a need for improved devices, systems, and techniques for delivering stimulation (e.g., chronic stimulation) to a nerve.

Additionally, many patients have a stimulation delivery device implanted without an initial pre-screening to inform the patient and/or care provider about the likely efficacy of the treatment. In some instances, patients have a stimulation delivery device implanted, but do not receive sufficient therapy efficacy to justify the cost and risks associated with the implantation surgery. Accordingly, there is a need for improved devices, systems, and techniques for non-surgical screening of patients to evaluate stimulation therapy efficacy before exposing patients to the costs and risks associated with device implantation surgery.

BRIEF SUMMARY

Described here are devices, systems, and methods for delivering stimulation therapy to a peripheral nerve (e.g., a sacral nerve), and mechanisms for controlling these devices and systems.

In some embodiments, the devices and systems may include an implantable pulse generator. The implantable pulse generator may comprise a non-transitory computer readable memory comprising instructions to calculate a heart rate parameter from cardiac data received from a cardiac sensor, calculate a disease activity parameter and a bodily activity parameter from activity data received from an activity sensor, determine an autonomic nervous system state based on the heart rate parameter, a physiological state based on the bodily activity parameter, and a disease state based on the disease activity parameter and adjust a nerve stimulation parameter of a stimulation signal based on the determined disease state. The implantable pulse generator may further comprise a microcontroller configured to execute the instructions.

In some embodiments, the implantable pulse generator may comprise a non-transitory computer readable memory comprising instructions to calculate a heart rate parameter from cardiac data received from a cardiac sensor, calculate a disease activity parameter from disease activity data received from a disease activity sensor, calculate a bodily activity parameter from bodily activity data received from a bodily activity sensor, determine an autonomic nervous system state, physiological state, and/or disease state of the patient based on the heart rate parameter, the disease activity parameter, and the bodily activity parameter, and adjust a sacral nerve stimulation parameter of a stimulation signal based on the determined autonomic nervous system state, physiological state, and/or disease state. The implantable pulse generator may further comprise a microcontroller configured to execute the instructions.

Methods for delivering a stimulation signal to a nerve of a patient may comprise receiving disease activity data from a disease activity sensor, determining a disease state of the patient based on the disease activity data, adjusting a nerve stimulation parameter of a stimulation signal based on the determined disease state, and applying an adjusted stimulation signal comprising the adjusted nerve stimulation parameter to the nerve of the patient. In some variations, the nerve may be the sacral nerve. In some instances, methods may further comprise calculating a disease activity parameter from the disease activity data. The disease activity parameter may comprise an inflammatory disease activity parameter or an oxidative stress activity parameter. In some variations, the disease activity parameter may comprise one or more of: an amplitude of inflammatory disease activity, a percentage of time with elevated inflammatory disease activity, an amplitude of oxidative stress activity, and a percentage of time with elevated oxidative stress activity.

In some variations, the disease activity sensor may be an implanted core body temperature sensor and the disease activity data may be core body temperature data. In some of these variations, the disease activity parameter may comprise an amplitude of the core body temperature data or a percentage of time with elevated core body temperature.

In some instances, methods may further comprise calculating a disease activity parameter from the disease activity data and calculating a heart rate parameter from the electrocardiographic or photoplethysmographic data. The disease state may be determined based on the disease activity parameter and an autonomic nervous system state may be determined based on the heart rate parameter. In some of these instances, the nerve stimulation parameter may be adjusted based on the disease state and the autonomic nervous system state.

In some embodiments, methods may further comprise receiving bodily activity data from a bodily activity sensor. In some variations, the disease activity sensor and the bodily activity sensor may be the same sensor. In some of these variations, the disease activity sensor and the bodily activity sensor may be a single implanted core body temperature sensor. In some variations, the disease state may be determined based on the disease activity data and the bodily activity data. In some of these variations, methods may further comprise calculating a disease activity parameter from the disease activity data and calculating a bodily activity parameter from the bodily activity data, where the disease state may be determined based on the disease activity parameter and the bodily activity parameter. The bodily activity parameter may comprise a respiratory activity parameter, a metabolic activity parameter, a gastrointestinal activity parameter, and a circadian rhythm parameter.

In some instances, the adjusted nerve stimulation parameter may comprise amplitude, frequency, pulse width, burst interval, or elapsed duration and/or the adjusted stimulation signal may be delivered using an implantable signal delivery device or a temporary signal delivery device. In some embodiments, the adjusted stimulation signal may be continuous. In other embodiments, the adjusted stimulation signal may be discontinuous. In some variations, the nerve may be the sacral nerve and application of the adjusted stimulation signal to the sacral nerve may suppress the production of pro-inflammatory cytokines, increase the production of anti-inflammatory cytokines, and/or reduce the sympathetic tone in a patient that has a chronic gastrointestinal disorder, a chronic auto-immune disease, or a metabolic disorder. In some instances, the methods may further comprise delivering a screening stimulation signal to the nerve using a temporary signal delivery device.

In some embodiments, methods for delivering a stimulation signal to a sacral nerve of a patient may comprise receiving electrocardiographic or photoplethysmographic data from a cardiac sensor, receiving temperature data from an implanted core body temperature sensor, determining a heart rate parameter from the electrocardiographic or photoplethysmographic data, determining a disease activity parameter and a bodily activity parameter from the temperature data, determining an autonomic nervous system state from the heart rate parameter, a physiological state from the bodily activity parameter and a disease state from the disease activity parameter, adjusting a nerve stimulation parameter of a stimulation signal based on the determined disease state; and applying an adjusted stimulation signal comprising the adjusted nerve stimulation parameter to the sacral nerve of the patient. In some variations, the nerve stimulation parameter may be adjusted based on the determined disease state and the autonomic nervous system state. In some variations, the nerve stimulation parameter may be adjusted based on the determined disease state and the physiological state. In some variations, the nerve stimulation parameter may be adjusted based on the determined disease state, the physiological state, and the autonomic nervous system state.

In some embodiments, systems for delivering an electrical stimulus to a nerve of patient may comprise a cardiac sensor, an activity sensor, an implantable signal delivery device configured to deliver a stimulation signal to the nerve, and an implantable pulse generator comprising a microcontroller. The microcontroller may be configured to receive cardiac data from the cardiac sensor and calculate a heart rate parameter from the cardiac data, receive activity data from the activity sensor and calculate a disease activity parameter and a bodily activity parameter from the activity data, determine an autonomic nervous system state, physiological state, and disease state of the patient based on the heart rate parameter, the disease activity parameter, and the bodily activity parameter, adjust a nerve stimulation parameter of a stimulation signal based on the determined autonomic nervous system state, physiological state, and/or disease state, and instruct the implantable signal delivery device to deliver an adjusted stimulation signal comprising the adjusted nerve stimulation parameter. In some variations, the cardiac sensor may be an implanted electrocardiographic electrode or external diagnostic device configured to measure values of the patient's heart rate. In some variations, the activity sensor may comprise at least one of an implanted core body temperature sensor, an implanted electromyographic electrode, an implanted movement sensor, an implanted non-enzymatic electrochemical sensor, an implanted oxygenation sensor, an implanted movement sensor, and external diagnostic device. In some embodiments, the adjusted nerve stimulation parameter may comprise a stimulation amplitude, a pulse width, a frequency, a burst interval, or an elapsed stimulation duration. In some instances, the system may further comprise a temporary signal delivery device configured to deliver a screening stimulation signal to the nerve.

In some embodiments, systems for delivering an electrical stimulus to a nerve of a patient may comprise a cardiac sensor, a disease activity sensor, a bodily activity sensor, an implantable signal delivery device configured to deliver a stimulation signal to the nerve, and an implantable pulse generator. The implantable pulse generator may comprise a non-transitory computer readable memory comprising instructions to calculate a heart rate parameter from cardiac data received from the cardiac sensor, calculate a disease activity parameter from disease activity data received from the disease activity sensor, calculate a bodily activity parameter from bodily activity data received from the bodily activity sensor, determine an autonomic nervous system state, physiological state, and/or disease state of the patient based on the heart rate parameter, the disease activity parameter, and the bodily activity parameter, and adjust a sacral nerve stimulation parameter of a stimulation signal based on the determined autonomic nervous system state, physiological state, and/or disease state. The implantable pulse generator may further comprise a microcontroller configured to execute the instructions.

BRIEF DESCRIPTION OF THE DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

FIG. 7 graphically illustrates the use of frequency-domain heart rate variability parameters extracted from electrocardiographic data, and particularly the power ratio of the low frequency and high frequency bands, observed during varying autonomic nervous system states. The upper plot illustrates an increase in the power ratio during food consumption-induced parasympathetic activation, while the lower plot illustrates a decrease in the power ratio during exercise-induced sympathetic activation.

FIG. 8 graphically illustrates changes in metabolic activity observed during several disease states and physiological states, collected continuously with a core body temperature sensor.

FIG. 10 is a block diagram depicting the learning phase of the algorithm.

DETAILED DESCRIPTION

Figure 1:
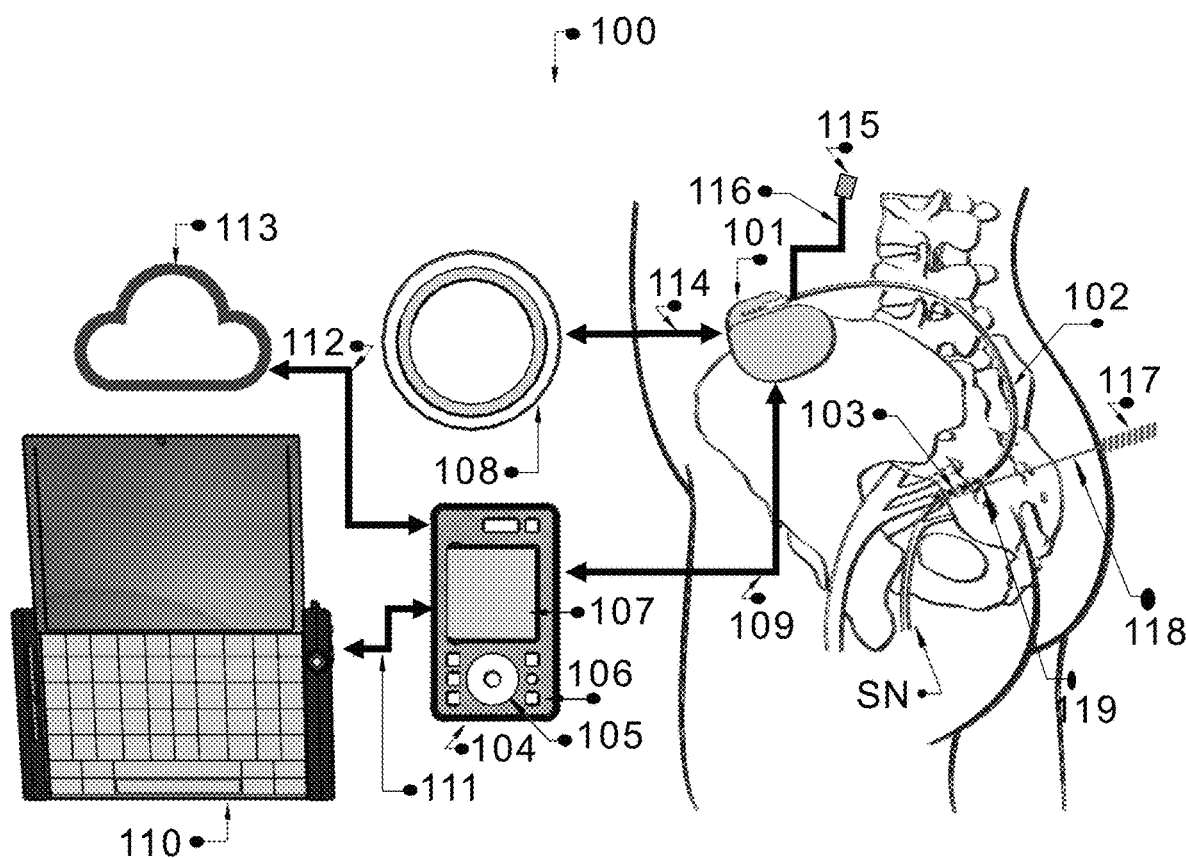
FIG. 1 is a schematic diagram of an illustrative system for providing non-surgical screening and stimulation therapy to a patient.

Described here are devices, systems, and methods for treating one or more chronic gastrointestinal disorders (such as irritable bowel syndrome, inflammatory bowel disease, ulcerative colitis, ulcerative proctitis, Crohn's disease, chronic constipation, chronic fecal incontinence, functional abdominal pain, gastroesophageal reflux disease, esophageal dysmotility, pseudo-obstruction, functional dyspepsia, gastroparesis, intestinal dysmotility, celiac disease, anorexia, colonic inertia, pancreatitis), chronic auto-immune diseases (such as autoimmune thyroid disease, ankylosing spondylitis, multiple sclerosis, myasthenia gravis, psoriasis, rheumatoid arthritis, Sjögren's syndrome, systemic lupus erythematosus, systemic sclerosis, juvenile idiopathic arthritis, Still's disease, macrophage activation syndrome, cytokine release syndrome, cytokine storm syndrome, hyperinflammation, acute respiratory distress syndrome, hemophagocytic lymphohistiocytosis, pneumonitis, chronic obstructive pulmonary disease, asthma, myocarditis), and metabolic disorders (such as type 2 diabetes mellitus, obesity, dyslipidemia, cardiometabolic disease, non-alcoholic fatty liver disease, chronic kidney disease, polycystic ovary syndrome, hypertension) by providing electrical stimulation therapy to a target peripheral nerve, for example, the sacral nerve. The devices, systems, and methods may generally provide for controllably stimulating the sacral nerve. For example, the devices, systems, and methods may adjust one or more stimulation parameters of a stimulation signal using data collected with one or more sensors. The devices, system and methods may calculate one or more physiological parameters and may determine one or more autonomic nervous system states, physiological states, and/or disease states. The devices, systems, and methods described here may facilitate parasympathetic activity in order to suppress the production of pro-inflammatory cytokines, to increase the production of anti-inflammatory cytokines, and/or to reduce the sympathetic tone in at least one chronic gastrointestinal disorder, chronic auto-immune diseases, metabolic disorder, or a combination of any of the above.

As used herein, the terms "stimulating" and "stimulation" refer generally to signals (e.g., electrical stimulus) applied to a patient to elicit a parasympathetic response in a nerve. Unless otherwise specified, the signals may have an activating/excitatory effect on a nerve, such as the sacral nerve. As used herein, the term "stimulator" applies generally to a device that generates and/or directs stimulation signals. Although described herein as stimulating the sacral nerve of a patient, the stimulators described here may also be used to stimulate other nerves.

As used herein, the term "physiological parameter" refers generally to a measurable metric extracted from data collected using a sensor. For example, measurable autonomic nervous system parameters (e.g., heart rate parameters) may be extracted from cardiac data (e.g., electrocardiographic or photoplethysmographic data), measurable disease activity parameters (e.g., inflammatory disease activity parameters, oxidative stress disease activity parameters) may be extracted from disease activity data (e.g., inflammatory disease activity data and oxidative stress activity data), and measurable bodily activity parameters (e.g., metabolic activity parameters, respiratory activity parameters, gastrointestinal activity parameters, circadian rhythm activity parameters) may be extracted from bodily activity data (e.g., metabolic activity data, respiratory activity data, gastrointestinal activity data, circadian rhythm data).

For example, the disease activity data may comprise inflammatory disease activity data and oxidative stress activity data collected using various sensors. In some variations, the inflammatory disease activity data may include long-term (e.g., about 6 hours, between about 3 hours and about 12 hours, between about 5 hour and about 8 hours, between about 9 hours and about 12 hours) averaged core body temperature data and/or the oxidative stress activity data may include tissue oxygen concentration data. The tissue oxygen concentration data may be collected with an implanted oxygenation sensor, with an implanted non-enzymatic electrochemical sensor, with an external diagnostic device, or with any other appropriate sensor. The bodily activity data may comprise metabolic activity data, respiratory activity data, gastrointestinal activity data and circadian rhythm data collected using various sensors. The metabolic activity data may include core body temperature data collected with, for example, an implanted core body temperature sensor and/or glucose data collected with, for example, an implanted non-enzymatic electrochemical sensor, a continuous glucose monitor (fully implanted or percutaneous), a test-strip based glucose monitor, or any other suitable device. The respiratory activity data may comprise chest wall movement data and/or diaphragm movement data collected with, for example, an implanted movement sensor, an external diagnostic device, or any other suitable sensor. The gastrointestinal activity data may include stomach movement data, small intestine movement data, and/or large intestine movement data collected with, for example, an implanted electromyographic electrode, an implanted movement sensor, an external diagnostic device, or any other suitable sensor. The circadian rhythm data may comprise electrocardiographic or photoplethysmographic data collected with, for example, an implanted or wearable electrocardiographic electrode or wearable photoplethysmographic electrode, electromyographic or photoplethysmographic data collected with, for example, an implanted or wearable electromyographic electrode or wearable photoplethysmographic electrode, and/or electrical or electrochemical skin data collected with, for example, an external (e.g., wrist-worn) diagnostic device.

Physiological parameters may be extracted using a variety of time-domain calculation methods and/or frequency-domain calculation methods. For example, with respect to the cardiac data, both time-domain calculation methods and frequency domain calculation methods may be used. The time-domain calculation may be used to measure the heart rate variability (HRV) in the beat-to-beat fluctuations in the rhythm of the heart from electrocardiographic or photoplethysmographic data. Among the HRV parameters, of particular interest is the period of heart rate turbulence (HRT) occurring immediately after a premature ventricular contraction. Time-domain HRT parameters may include HRT onset, referring to an early acceleration of the sinus rhythm, and HRT slope, referring to a slower gradual later deceleration. The frequency-domain calculation may then be applied to the HRV data to calculate the power of the low frequency (LF) band, the power of the high frequency (HF) band, and the LF/HF power ratio. The power of the LF band (0.04 Hz to 0.15 Hz) measures the sympathetic influence on the heart, while the power of the HF band (0.15 Hz to 0.40 Hz) measures the parasympathetic influence on the heart. The LF/HF power ratio indicates the functional prevalence of the sympathetic activity over the parasympathetic activity. Thus, the heart rate parameters may include a time-domain parameter (e.g., average heart rate, heart rate variability, HRT onset, HRT slope) and/or a frequency-domain parameter (e.g., power of the LF band, power of the HF band, LF/HF power ratio).

With respect to the disease activity data, the time-domain calculation may be used to determine an amplitude of the disease activity data and/or a percentage of time with elevated disease activity. For example, for the inflammatory disease activity data, the time-domain calculation may be used to determine an amplitude of inflammatory disease activity from long-term (e.g., 6 hours) averaging of core body temperature data and/or a percentage of time with elevated inflammatory disease activity (e.g., elevated core body temperature), while for the oxidative stress activity data, the time-domain calculation may be used to determine an amplitude of oxidative stress activity from long-term (e.g., 6 hours) averaging of tissue oxygen concentration data and/or a percentage of time with elevated oxidative stress activity (e.g., elevated tissue oxygen concentration). Thus, the disease activity parameters may comprise an amplitude of disease activity data (e.g., an amplitude of inflammatory disease activity or oxidative stress activity) and a percentage of time with elevated disease activity (e.g., elevated inflammatory disease activity or elevated oxidative stress activity). Disease activity may be considered elevated when it is at least about 10%, about 15%, about 20%, about 25% about 30%, about 35%, about 40%, about 50%, between about 10% and about 20%, about 20% and about 30%, about 30% and about 40% or more above the normal value or range of values.

With respect to the bodily activity data, the time-domain calculation may be used to determine an amplitude of the bodily activity data and/or a percentage of time with elevated bodily activity. For example, for the metabolic activity data, the time-domain calculation may be used to determine an amplitude of metabolic activity and/or a percentage of time with elevated metabolic activity from short-term (e.g., 1 hour) averaged core body temperature data and/or short-term (e.g., 1 hour) averaged glucose data. For respiratory activity data, the time-domain calculation may be used to determine a percentage of time in inspiration and expiration phases and the frequency-domain calculation may be used to determine a respiratory rate from chest wall movement data and/or diaphragm movement data. For gastrointestinal activity data, the time-domain calculation may be used to determine an amplitude of gastrointestinal activity and/or a percentage of time with elevated gastrointestinal activity and the frequency-domain calculation may be used to determine an intestinal contraction rate from stomach movement data and/or small intestine movement data and/or large intestine movement data. For the circadian rhythm data, the time-domain calculation may be used to determine a percentage of time in a circadian rhythm phase (e.g., awake, asleep) from electrocardiographic or photoplethysmographic data, electromyographic data, electrical skin data, and/or electrochemical skin data. Thus, the bodily activity parameters may comprise an amplitude of bodily activity data (e.g., amplitude of metabolic activity, amplitude of respiratory activity, amplitude of gastrointestinal activity) and a percentage of time with elevated bodily activity (e.g., elevated metabolic activity, elevated respiratory activity, elevated gastrointestinal activity) or at a particular circadian rhythm phase (e.g. percentage of time in "awake" phase, percentage of time in "asleep" phase). Bodily activity may be considered elevated when it is at least about 10%, about 15%, about 20%, about 25% about 30%, about 35%, about 40%, about 50%, between about 10% and about 20%, about 20% and about 30%, about 30% and about 40% or more above the normal value or range of values.

As used herein, the term "autonomic nervous system state" refers generally to a category assigned to a particular level of sympathetic or parasympathetic activity. For example, the autonomic nervous system state of "parasympathetic activation" refers to activation of parasympathetic activity, for example during food consumption. This can be contrasted with the autonomic nervous system state of "sympathetic activation", which refers to activation of sympathetic activity, for example during physical exercise.

As used herein, the term "physiological state" refers generally to a category assigned to a particular level of activity of one or more internal organs or systems in the patient's body. For example, the physiological state of "food consumption" refers to short-term activation of metabolic activity following consumption of some type of food (e.g. liquid, light meal, or heavy meal). This can be contrasted with the physiological state of "fasting", characterized by a medium level of metabolic activity, and to the physiological state of "sleep", characterized by a low level of metabolic activity.

As used herein, the term "disease state" refers generally to a category assigned to a particular level of disease activity. In one example, the disease state of "flare" refers to increased inflammatory disease activity in any inflammatory, auto-immune, or metabolic disease. For example, in some variations where "flare" refers to increased inflammatory disease activity in an inflammatory disease, the inflammatory disease may include irritable bowel syndrome, inflammatory bowel disease, ulcerative colitis, ulcerative proctitis, and Crohn's disease. In another example, the disease state of "oxidative stress" refers to increased inflammatory disease activity in any inflammatory, auto-immune, or metabolic disease. For example, in some variations where "oxidative stress: refers to increased inflammatory disease activity in an inflammatory disease, the inflammatory disease may include irritable bowel syndrome, inflammatory bowel disease, ulcerative colitis, ulcerative proctitis, Crohn's disease, chronic constipation, chronic fecal incontinence, functional abdominal pain, gastroesophageal reflux disease, esophageal dysmotility, pseudo-obstruction, functional dyspepsia, gastroparesis, intestinal dysmotility, colonic inertia, pancreatitis. Other disease states include "early inflammatory response", "late inflammatory response", "hypoxia", "no flare", and "no oxidative stress".

As used herein, the term "stimulation parameter" refers generally to a setting of the electrical stimulation therapy applied to a nerve (e.g., sacral nerve) using a signal delivery device (e.g., an implantable signal delivery device or a temporary signal delivery device). For example, stimulation parameters may include a stimulation amplitude, a pulse width, a frequency, a burst interval, an elapsed duration, and/or other suitable settings of the electrical stimulation therapy. As used herein, the term "stimulation signal" refers to the output of the stimulator that is generated based on the combination of stimulation parameters.

In some variations of the devices, systems, and methods described herein, the amplitude of the pulses may be between about 0.1 mA and about 30 mA, the width of the pulses may be between about 100 microseconds and about 2 milliseconds, and/or the frequency of the pulses may be between about 1 Hz and about 100 Hz. In some embodiments, the stimulation signal may comprise rectangular pulses and/or complex electrical pulses. In variations in using complex electrical pulses, the complex electrical pulses may comprise multi-level pulses, biphasic pulses, non-rectangular pulses, pulses with varying inter-pulse intervals, pulses with varying amplitude, or a combination thereof.

The therapy may be applied continuously or intermittently (e.g. with a therapy session period of about 0.1 to about 8 hours and an inter-therapy session period of about 16 to just below 24 hours (e.g., 23.9 hours, from about 23.5 hours to about 23.9 hours). For example, in some variations, the therapy session period may be about 1 hour, about 2 hours, about 3 hours, about 4 hours, from about 1 hour to about 2 hours, from about 1 hour to about 4 hours, or from about 2 hours to about 4 hours. During the therapy application, delivery of the stimulation signal may be continuous or discontinuous. For example, in some variations, the system may deliver the stimulation signal discontinuously with a train of pulses applied during a train duration, and the trains of pulses may be separated by an inter-train duration when pulses are not delivered. The discontinuously-delivered stimulation signal may have a duty cycle represented as a train duration portion of a therapy session period. In some variations, the duty cycle may be from about 0.1% to about 50%, for example, 1%, 5%, 10%, 15%, or 20%.

Systems

The nerve stimulation systems described here may generally comprise a sensor (e.g., wearable and/or implantable), a nerve (e.g., sacral nerve) stimulation device (e.g., an implantable pulse generator and/or an external pulse generator), one or more signal delivery devices (implantable and/or temporary), and an external programmer. In some variations, the systems may further comprise a computer, a power charger for the nerve stimulation device, and/or a server. FIG. 1 schematically illustrates one embodiment of a sacral nerve stimulation system 100. In that embodiment, the stimulation system 100 may comprise an implantable pulse generator 101, an implantable signal delivery device 102, an external programmer 104, a charging antenna 108, a computer 110, a cloud server 113, a temporary signal delivery device 117, and a sensor 115 (e.g., wearable and/or implantable). The sacral nerve stimulation system 100 is shown in FIG. 1 positioned relative to the general anatomy of the sacral nerve (labeled "SN" in FIG. 1) of a patient. In particular, the implantable signal delivery device 102 is depicted implanted within a sacral foramen of a patient, and the implantable pulse generator 101 is depicted implanted in a subcutaneous pocket in the lower back. In some variations, an external pulse generator may be used instead of an implantable pulse generator 101.

Pulse Generator

As mentioned above, the systems described here may comprise a nerve stimulation device, for example, an implantable pulse generator and/or an external pulse generator. The nerve stimulation device may be configured to generate and transmit stimulation signals to the implantable signal delivery device 102 and/or the temporary signal delivery device 117. The pulse generator may also be configured to receive data from the sensor 115.

The pulse generator may comprise a microcontroller interconnected with non-transitory computer-readable memory containing the instructions for the microcontroller, and further connected with input/output devices (e.g., wired or wireless transceivers), power management circuitry, and/or other suitable electrical components. The computer-readable memory may comprise volatile and/or nonvolatile memory, e.g., read-only memory (ROM), random access memory (RAM), magnetic memory, flash memory, and/or others. In some embodiments, the pulse generator 101 may also comprise specific hardware components having hard-wired logic (e.g., field-programmable gate arrays) for performing the operations, methods, or processes or with any combination of programmed data processing components and specific hardware components. In some variations, the pulse generator 101 may transmit stimulation signals to the signal delivery device 112 using an Ultra High Frequency (UHF) band (e.g., Bluetooth, BLE, Wi-Fi, and ANT+ protocols operating at 2.4-2.5 GHz band), Super High Frequency (SHF) band (e.g., Wi-Fi protocols operating at 3.6-3.7 GHz and 5.1-6.0 GHz bands), and/or a Very High Frequency (VHF) band.

Figure 2:
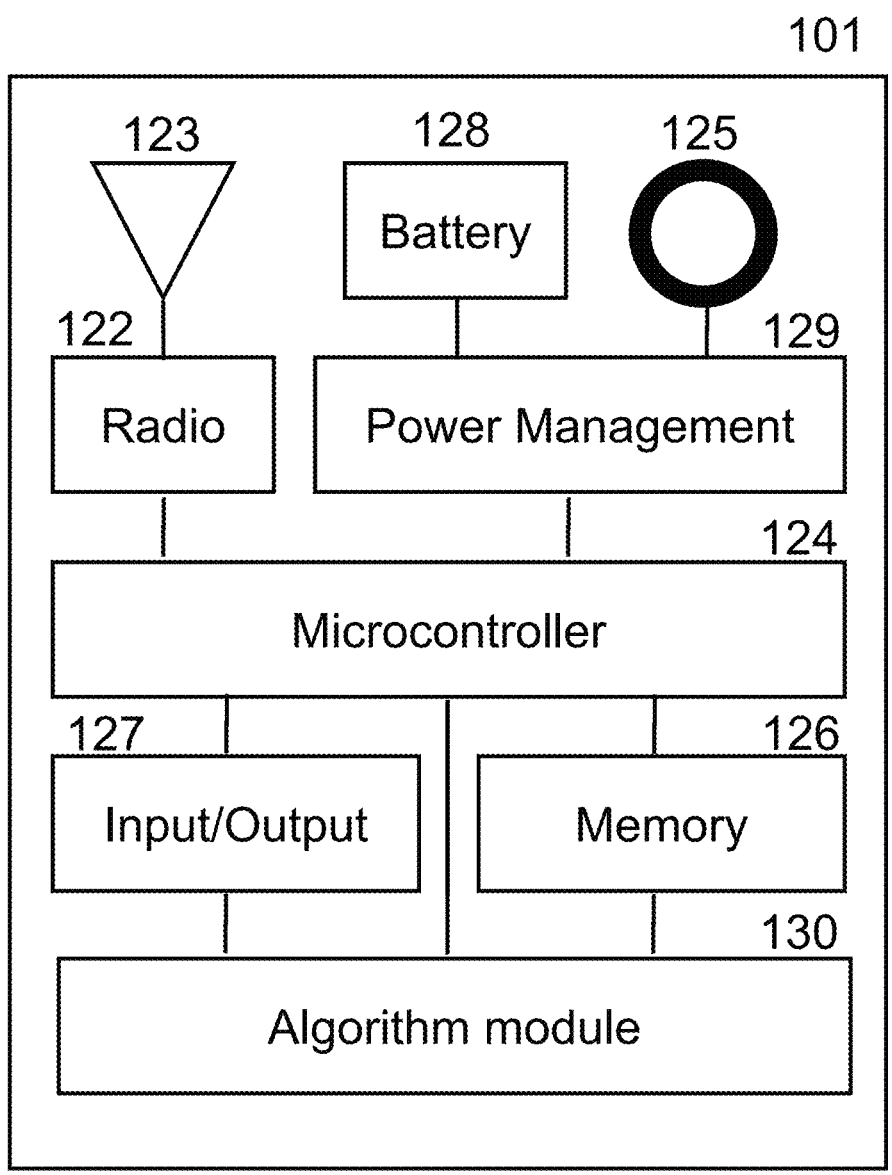
FIG. 2 is a block diagram depicting components of an exemplary pulse generator.

FIG. 2 is a functional block diagram illustrating components of the pulse generator 101 of FIG. 1. As shown there, the pulse generator 101 may comprise: a radio 122, a radio antenna 123, a microcontroller 124, a charging coil 125, a memory module 126, an input/output module 127, a battery 128, a power management circuit 129, and an algorithm module 130. The radio antenna 123 may create a bidirectional wireless data link 109 to communicate with the external programmer 104, and the charging coil 125 (e.g., an induction coil) may create a bidirectional wireless power communication link 114 with the wireless charging antenna 108 for recharging the battery 128 via the power management circuit 129. The microcontroller 124 may be coupled to the input/output module 127 and the memory module 126.

The pulse generator 101 may generally be configured to receive data from the one or more sensors, calculate physiological parameters from the data received, determine an autonomic nervous system state, physiological state, and/or disease state from the physiological parameters, adjust a stimulation parameter, and instruct the implantable signal delivery device 102 and/or temporary signal delivery device 117 to deliver a stimulation signal comprising the adjusted stimulation parameter. The pulse generator 101 may also be configured to establish correlation weights between physiological parameters and autonomic nervous system states, physiological states, and disease states during a learning phase. The pulse generator 101 may be configured to subsequently automatically start stimulation, stop stimulation, and/or adjust one or more stimulation parameters based, at least in part, on the correlation weights between physiological parameters and autonomic nervous system states, physiological states, and/or disease states learned during a learning phase of the algorithm in the algorithm module 130, as will be discussed in more detail herein, and the current physiological parameters and autonomic nervous system states, physiological states, and/or disease states of the patient.

For example, in a variation in which the system comprises a cardiac sensor and an implanted core body temperature sensor, the pulse generator 101 may be configured to receive cardiac data from the cardiac sensor and calculate a heart rate parameter (e.g., a heart rate) from the cardiac data, receive disease activity data from the implanted core body temperature sensor and calculate a disease activity parameter (e.g., amplitude of inflammatory disease activity) from the disease activity data, receive bodily activity data from the implanted core body temperature sensor and calculate and a bodily activity parameter (e.g. amplitude of metabolic activity) from the bodily activity data, determine an autonomic nervous system state, physiological state, and/or disease state of the patient based on the physiological parameters (e.g., the heart rate, the amplitude of inflammatory disease activity, the amplitude of metabolic activity), adjust a stimulation parameter based on the determined autonomic nervous system state, physiological state, and/or disease state, and instruct the implantable signal delivery device 102 to deliver an adjusted stimulation signal comprising the adjusted nerve stimulation parameter. In this variation, the disease activity sensor and the bodily activity sensor may be the same implanted core body temperature sensor or they may be different implanted core body temperature sensors. Put another way, the disease activity data and the bodily activity data may both be temperature data measured by the same temperature sensor (e.g., an implanted core body temperature sensor).

While the therapy system 100 is described above with the algorithm module 130 residing in the pulse generator 101, it need not. For example, in some variations, the external programmer 104, the computer 110, and/or the cloud server 113 may comprise the algorithm module 130, and the pulse generator 101 may transfer current sensor data and/or calculated physiological parameters to the external programmer 104, the computer 110, and/or the cloud server 113 via the bidirectional wireless data link 109. In some variations, portions of the algorithm module 130 may be contained in the pulse generator 101 and one or more of the external programmer 104, the computer 110, and the cloud server 113. In some variations, a database of sensor measurements, physiological parameters, autonomic nervous system states, physiological states, and/or disease states, and/or correlation weights may be stored in the memory module 126 and may be uploaded to or downloaded from the external programmer 104, the computer 110, and the cloud server 113.

The power management circuit 129 may comprise a frequency modulator, an amplitude modulator, and/or other suitable circuitry for modulating inductive protocols. The microcontroller 124 may be configured to provide control signals to and receive data from the radio 122 and to communicate with the power management circuit 129. In certain embodiments, the microcontroller 124 may include a detector or a decoder with associated software and/or firmware to perform detection/decoding functions and process received signals. The memory module 126 may include volatile and/or nonvolatile storage. The memory module 126 may be configured to store data received from, as well as instructions for, the microcontroller 124. The input/output module 127 may include logic components that receive and interpret input from the external programmer 104 as well as logic components that output information to the external programmer 104 (FIG. 1). The microcontroller 124, the input/output module 127, and the memory module 126 may communicate with the algorithm module 130. The algorithm module 130 may contain a computer program, with its source code written in a conventional programming language (e.g., the C++ or C programming languages) and may be executed by the microcontroller 124.

Figure 3:
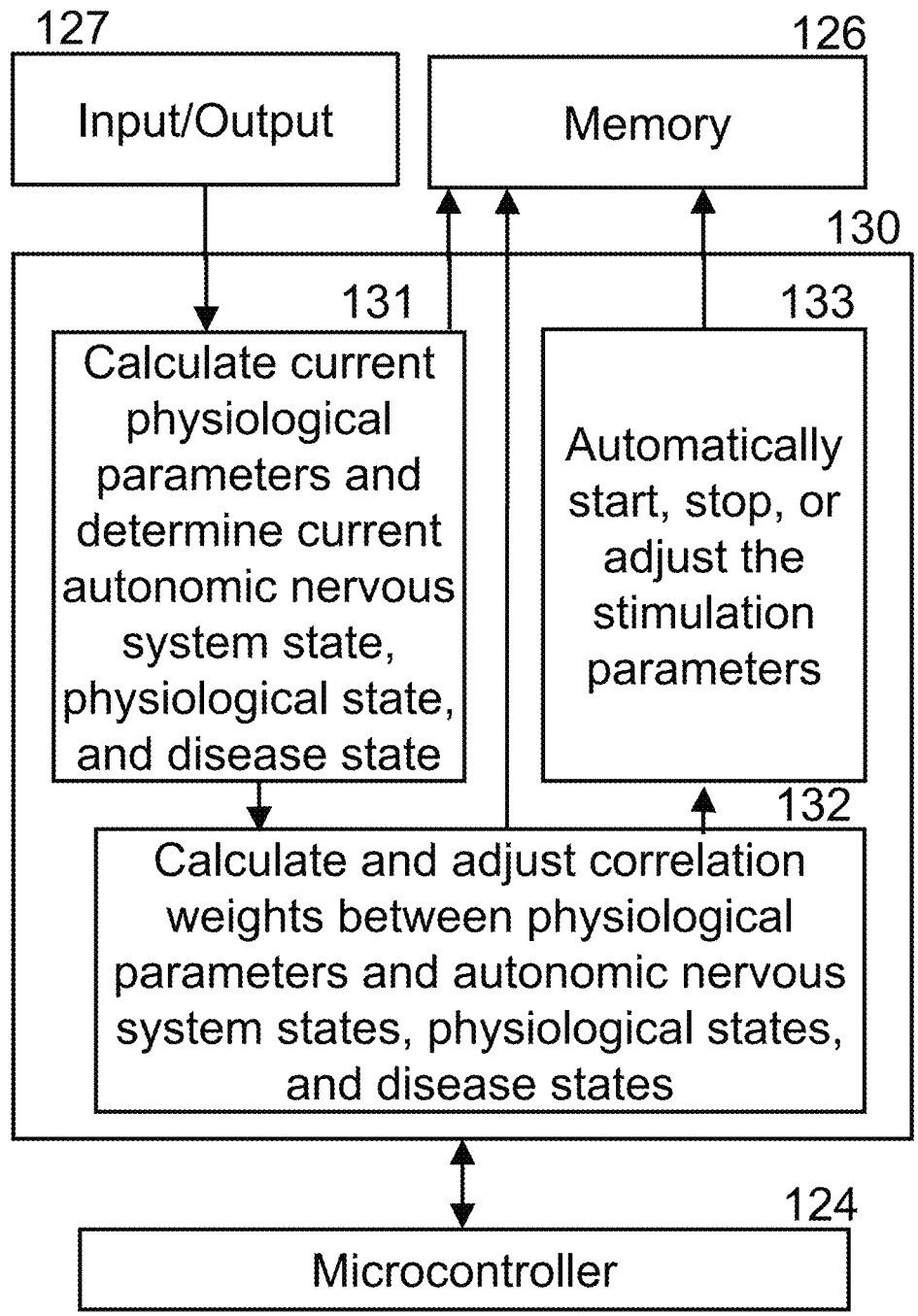
FIG. 3 is a block diagram depicting components and software modules of an exemplary pulse generator.

FIG. 3 is a block diagram showing the algorithm module 130 of the pulse generator 101 of FIG. 2. For the ongoing monitoring of the physiological parameters, the pulse generator 101 (e.g., the algorithm module) may periodically receive the sensor data from the input/output module 127, calculate current physiological parameters, and determine a current autonomic nervous system state, physiological state, and/or disease state 131. The pulse generator 101 may use the current physiological parameters and autonomic nervous system states, physiological states, and/or disease states 131 to calculate and adjust correlation weights between physiological parameters and autonomic nervous system states, physiological states, and/or disease states 132. The current physiological parameters, autonomic nervous system states, physiological states, and/or disease states, and correlation weights may be added to the database in the memory module 126. Any of a variety of suitable database organizations may be utilized, including a flat file system, hierarchical database, relational database, or distributed database. The microcontroller 124 may periodically execute the algorithm module on a continuous, ongoing basis (or as needed or requested) to recognize any trends in the collected information which may, in some instances, be used to automatically start, stop, or adjust the stimulation parameters 133. Current stimulation parameters may be added to the database in the memory module 126. As will be described in more detail herein, the algorithm may have two phases—a learning phase and an automatic operation phase. Generally, the algorithm may calculate or otherwise receive the physiological parameter data and correlate it with the patient-provided autonomic nervous system states, physiological states, and/or disease states during the learning phase. In the automatic operation phase, the algorithm may calculate or otherwise receive the physiological parameter data and start, stop, or adjust the signal delivery based on correlation weights between the physiological parameters and autonomic nervous system states, physiological states, and/or disease states, and the signal parameters assigned to specific autonomic nervous system states, physiological states, and/or disease states established during the learning phase.

In the learning phase, an autonomic nervous system state, physiological state, and/or disease state may be defined by and/or received from a patient, determined by the algorithm, or both. In the automatic operation phase, an autonomic nervous system state, physiological state, and/or disease state may be determined by the system (e.g., algorithm) alone, without patient input. Each autonomic nervous system state, physiological state, and/or disease state may be associated with an initial stimulation program and/or initial stimulation signal parameters, which may be preset by a clinician, a device company representative, and/or other member of authorized personnel and may, in instances, later be adjusted by the patient. In some instances, it may be beneficial for the system (e.g., the algorithm) to accurately distinguish disease states from physiological states, as this may improve therapy efficacy and/or may reduce the frequency and/or severity of unwanted side effects. For example, in some instances, a patient may have an elevated core body temperature when he or she has an inflammatory response (e.g., in a disease state of "flare") and when he/she is eating a meal (e.g., in a physiological state of "meal consumption"). The algorithm may distinguish between the "flare" and "meal consumption" states by considering values of other physiological parameters (e.g. autonomic nervous system parameters, disease activity parameters, bodily activity parameters).

During the learning phase, the algorithm may be trained using a machine learning method, such as, for example, backpropagation, by correlating values of physiological parameters with autonomic nervous system states, physiological states, and/or disease states. In some variations, the machine learning method may be an artificial neural network, where the physiological parameters form input layer nodes, the autonomic nervous system states, physiological states, and/or disease states form an output layer node, and the correlation weight values between the physiological parameters and the autonomic nervous system states, physiological states, and/or disease states form the hidden layer nodes. The algorithm may calculate the correlation weights using one of the following classification methods: thresholding, multiple linear regression, k nearest neighbor, linear discriminant analysis, feedforward neural network, convolutional neural network, random forest, logistic regression, or support vector machine. In some embodiments, the algorithm may use an electrical circuit embedded in the pulse generator 101, in the external programmer 104, and/or in another external device.

A clinician, a device company representative, and/or other member of authorized personnel may program the implantable pulse generator by setting up one or more stimulation programs for the patient and allowing the patient to adjust the stimulation parameters. Once the programs are established, the patient may have the ability to change only a subset of parameters in an individual program, e.g., only an amplitude, only a pulse width, or only a frequency. Also, at the initial setup, the clinician, the device company representative, and/or other member of authorized personnel may initialize the individual sensors with "normal" or expected values. In some variations, the clinician, the device company representative, and/or other member of authorized personnel may also set a confidence level for correlation weights in the algorithm, for example, from about 80% to about 99%, to indicate the end of the learning phase. The clinician, the device company representative, and/or other member of authorized personnel may also set a delta change threshold for individual sensors, e.g., 5-10% of the signal average, for detecting abnormal operations of the pulse generator and/or sensor inputs that are outside an expected range, as described in more detail below.

During an embodiment of the learning phase, the individual sensors may be reset and normalized with initial values, and the implantable pulse generator may be instructed by a clinician, the device company representative, and/or other member of authorized personnel to initiate the learning phase of the algorithm. In the learning phase, the pulse generator (e.g., via the algorithm) may continuously or intermittently monitor the patient's physiological parameters (e.g. autonomic nervous system parameters, disease activity parameters, bodily activity parameters), may determine the autonomic nervous system states (e.g., "sympathetic activation" or "parasympathetic activation"), the physiological state (e.g. "food consumption" or "fasting") and/or the disease state (e.g. "flare" or "oxidative stress"), and may adjust the stimulation parameters. In addition, the patient, the clinician, the device company representative, and/or other member of authorized personnel may change the stimulation program and/or the stimulation parameters.

In some variations of the learning phase, in response to the changed autonomic nervous system state, physiological state, and/or disease state (e.g., provided by the patient), the algorithm may calculate current physiological parameters, determine the correlation weights with the patient-provided autonomic nervous system state, physiological state, and/or disease state, and activate a preset or adjusted stimulation program or stimulation parameters. While recording the correlation weights, the algorithm may build a database of correlation weights between multiple physiological parameters and multiple autonomic nervous system states, physiological states, and/or disease states and of preset and/or adjusted stimulation programs/parameters associated with particular autonomic nervous system states, physiological states, and/or disease states.

In one example, the patient-provided physiological state may be "during heavy meal" and the measured physiological parameters may be: "LF power" is high and "HF power" is low. The pulse generator may have been pre-programmed with a preset stimulation program, for example, Program 1, which corresponds to the physiological state "during heavy meal." Once this physiological state is detected (e.g., by receiving user input), the system may deliver Program 1. After an elapsed period of time, for example, two hours, the physiological state may have changed to, for example, "after heavy meal." The system may detect this change via patient reporting (e.g., the patient instructs the system that the physiological state has changed) or using preset time intervals for particular physiological states. For example, in some variations, the duration of particular states may be preset by a clinician, a device company representative, a patient, or the like. In the example described here, the duration of the physiological state "during heavy meal" may have been preset to two hours. At that time, the measured physiological parameters may be: "LF power" is medium and "HF power" is medium. The preset stimulation Program 1 may then be stopped. Although the stimulation may be stopped, the algorithm may continue to monitor for changes in physiological parameters, patient-provided physiological and/or disease states, and/or patient adjustment of stimulation parameters.

In another example, the patient-provided disease state may be "flare" and the measured physiological parameter "core body temperature" may be "high". The pulse generator may have been pre-programmed with a preset stimulation program, for example, Program 2, which corresponds to the disease state "flare." Once this disease state is detected (e.g., by receiving user input), the system may deliver Program 2. After an elapsed period of time, for example, six hours, the disease state may have changed to, for example, "no flare." The system may detect this change via patient reporting (e.g., the patient instructs the system that the disease state has changed) or using preset time intervals for particular disease states. For example, in some variations, the duration of particular states may be preset by a clinician, a device company representative, a patient, or the like. In the example described here, the duration of the disease state "flare" may have been preset to six hours. At that time, the measured physiological parameter "core body temperature" may be "medium" or "low". The preset stimulation Program 2 may then be stopped. Although the stimulation may be stopped, the algorithm may continue to monitor for changes in physiological parameters, patient-provided physiological and/or disease states, and/or patient adjustment of stimulation parameters.

The database of correlation weights and adjusted stimulation parameters for each autonomic nervous system state, physiological state, and disease state may be continuously or intermittently populated and adjusted as the algorithm learns, while the clinician and patient are in full manual control of the stimulation programs and/or parameters. Referring again to the above example, if at any time the clinician or patient adjusts the parameters of Program 1 during the physiological state "heavy meal consumption", the algorithm may populate the database with the current physiological parameters, the physiological state "during heavy meal", and current Program 1 stimulation parameters (e.g., frequency, pulse width and amplitude). Over a period of time (e.g., 1 week, 2 weeks, 3 weeks, 1 month, 2 months, 1 week-3 weeks, 2 weeks-4 weeks, 1 month-2 months, or the like), the implantable pulse generator may collect sufficient data to meet the preset confidence levels for correlation weights and may enter the automatic operation phase.

In some variations, the learning phase may comprise sub-phases for certain physiological states, such as autonomic nervous system states (e.g. "sympathetic activation" and "parasympathetic activation"), disease states (e.g. "flare", "oxidative stress", "early inflammatory response", "late inflammatory response", "hypoxia"), or physiological states (e.g. "during heavy meal" and "after heavy meal"). For example, in some embodiments, the learning phase may comprise a first sub-phase, an autonomic nervous system state sub-phase, a second sub-phase, a disease state sub-phase, and a third sub-phase, a physiological state sub-phase. In the autonomic nervous system state sub-phase, the implantable pulse generator may utilize only the autonomic nervous system parameters (e.g. LF power, HF power, LF/HF ratio, as described above) for training (e.g., as input layer nodes) the algorithm. In the disease state sub-phase, the implantable pulse generator may utilize the disease activity parameters (e.g., amplitude of inflammatory disease activity) in addition to the autonomic nervous system parameters for training the algorithm. In the physiological state sub-phase, the implantable pulse generator may utilize the bodily activity parameters (e.g., amplitude of metabolic activity, amplitude of respiratory activity, amplitude of gastrointestinal activity, circadian rhythm phase) in addition to the autonomic nervous system parameters for training the algorithm.

In some instances, the system may comprise a body-worn (i.e., not implanted) sensor (e.g., electrocardiographic or photoplethysmographic electrode) to measure electrical or optical activity of the heart (e.g., autonomic nervous system parameters). In these variations, the system may perform or begin to perform the autonomic nervous system sub-phase prior to implantation of an implantable pulse generator, such as pulse generator 101. For example, the system may comprise a wearable electrocardiographic or photoplethysmographic electrode, which may collect electrocardiographic or photoplethysmographic data and send the data to an external pulse generator or the external programmer 104. This data may be used to train the algorithm module based on the autonomic nervous system parameters. In this example, the external pulse generator, external programmer, the computer, or the cloud server may initially comprise the algorithm module and the algorithm module may later be transferred to the implantable pulse generator 101. In some instances, performance of the autonomic nervous system state sub-phase prior to implantation may allow for an initial pre-selection of patients who may be suitable for implantation and/or may reduce the use of the battery of the implantable pulse generator (as it may only be used during the disease state sub-phase and/or physiological state sub-phase).

During the automatic operation phase, the algorithm may use the information in the populated database to determine the autonomic nervous system states, physiological states, and/or disease states and set the stimulation parameters, given certain combinations of physiological parameters. For example, when the implantable pulse generator detects a change in measured HRV parameters, (e.g., that "LF power" is high and "HF power" is low), the algorithm may automatically determine the autonomic nervous system state, physiological state, and/or disease state, (e.g., "during heavy meal"). As a result, the implantable pulse generator may automatically turn on the best-matching stimulation program or stimulation parameters determined during the learning phase, rather than using the initial stimulation parameters.

The length of time required to meet the confidence levels may be patient-dependent and may be influenced by one or more factors, including for example, the number and frequency of a clinician's and/or a patient's selections, and/or other factors that may vary for each patient depending on the patient's satisfaction level. Once the implantable pulse generator has met or exceeded the confidence levels, the algorithm may enter the automatic phase for that autonomic nervous system state, physiological state, or disease state.

The pulse generator 101 need not enter the automatic operation phase for all autonomic nervous system states, physiological states, and/or disease states simultaneously. In particular, the pulse generator 101 may enter the automatic operation phase for one autonomic nervous system state, physiological state, or disease states state but may remain in the learning phase for one or more other autonomic nervous system states, physiological states, and/or disease states. Put another way, the confidence level for correlation weights between all physiological parameters and all autonomic nervous system states, physiological states, and/or disease states need not be achieved before the device can enter the automatic operation phase for a certain autonomic nervous system state, physiological state, or disease state. As an example, if the algorithm reaches the preset confidence level for the correlation weights to determine the physiological states "during heavy meal" and "after heavy meal", then the implantable pulse generator may proceed into the automatic operation phase for these states only, while the device may continue to operate in the learning phase for other autonomic nervous system states, physiological states, and disease states.

When the implantable pulse generator enters the automatic operation phase (and optionally in the learning phase), it may automatically change the stimulation program and/or stimulation parameters for the patient. In some variations, the system may alert the patient before automatically making an adjustment by, for example, displaying a message, illuminating a status light, or producing a discrete vibration on an external programmer, a combination thereof, or the like. In some variations, this alert feature may be switched-off, removed over time, or eliminated entirely.

The implantable pulse generator may continuously or intermittently check for a change in one or more measured physiological parameters, a change in stimulation program, and/or a change in stimulation parameters that are outside the preset delta change thresholds. If such a change is detected and is outside the delta change thresholds, in certain embodiments, the implantable pulse generator may alert the patient that such a change has occurred. In certain cases, the system may notify the clinician directly by sending an automatic note (e.g. email, text message, or otherwise as appropriate) of the change in the physiological parameters and/or stimulation parameters. For example, such a change may include a physiological parameter value or a patient-adjusted amplitude that is outside preset delta change thresholds. In response, the patient may override this alert, and the algorithm may record the event as a new database entry and start to learn more about this physiological parameter and/or stimulation parameter. In other embodiments, the patient may turn off the stimulation therapy and see a clinician. The clinician may then troubleshoot and adjust the therapy for the patient. The implantable pulse generator may re-enter the learning mode for these physiological parameters and/or stimulation parameters.

In some variations, the implantable pulse generator may automatically start and/or stop stimulation by monitoring an elapsed time. For example, in some variations in which the implantable pulse generator may automatically start stimulation, the implantable pulse generator may monitor an elapsed time since application of a stimulation signal and may compare the elapsed time to a predetermined time duration or threshold (e.g., if elapsed time is below the predetermined time threshold, stimulation will not begin; if elapsed time is at or above the predetermined time threshold, stimulation will automatically be applied). In some variations in which the implantable pulse generator may automatically stop stimulation, the implantable pulse generator may monitor an elapsed time since beginning stimulation or application of a stimulation signal and may compare the elapsed time to a predetermined time duration or threshold (e.g., if elapsed time is below the predetermined threshold, stimulation will not be stopped; if elapsed time is at or above the predetermined time threshold, stimulation will automatically be stopped).

Signal Delivery Devices

Referring back to FIG. 1, the system 100 may comprise one or more (e.g., two, three, four, or more) signal delivery devices. For example, as shown in FIG. 1, the system 100 may comprise an implantable signal delivery device 102 and one or more temporary signal delivery devices 117. The implantable signal delivery device 102 may comprise a stimulation electrode 103, and may be operably coupled to the pulse generator 101, for example, via a wired or wireless link. The temporary signal delivery device 117 may also comprise a stimulation electrode 119 and may be operably coupled to the pulse generator 101 (e.g., via a wired or wireless link). In some variations, the system may comprise a plurality of temporary signal delivery devices 117, which may be used sequentially and replaced periodically, as will be described in more detail herein. The implantable signal delivery device 102 and/or temporary signal delivery device 117 may be used to apply a stimulation signal to a nerve (e.g., sacral nerve) using the stimulation electrodes 103, 119.

In variations in which the temporary signal delivery device 117 is utilized during a screening phase, as will be described in more detail herein, the temporary signal delivery device 117 may be used to apply a screening stimulation signal.

Figure 11A:
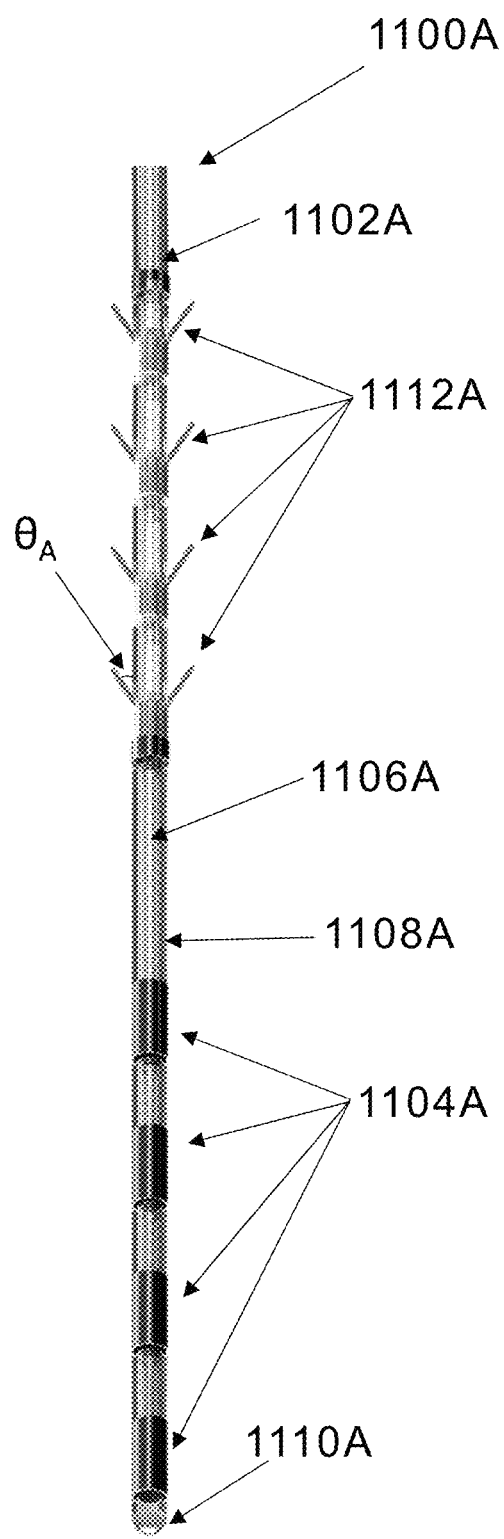
FIGS. 11A and 11B depict illustrative variations of an implantable signal delivery device.
Figure 11B:
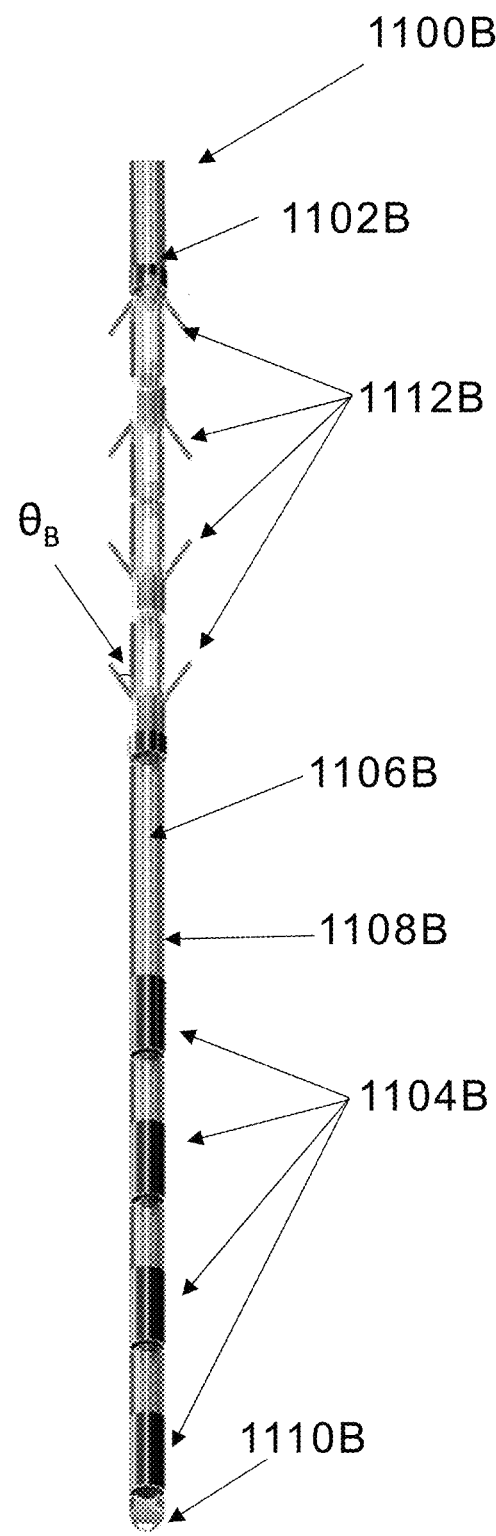

FIGS. 11A and 11B depict embodiments of an implantable signal delivery device 1100A, 1100B. As shown there, the implantable signal delivery device 1100A, 1100B may comprise an elongated body 1102A, 1102B and one or more stimulation electrodes 1104A, 1104B (e.g., two, three, four, five, or more) (depictured in FIG. 1 as stimulation electrode 103). The stimulation electrodes 1104A, 1104B may be positioned on an external surface of the elongate body 1102A, 1102B, for example, at or near a distal end of the elongated body 1102A, 1102B, and each may comprise a contact surface made from a metal (e.g., stainless steel, platinum, iridium), metal alloy or conductive polymer for delivering electrical current to a nerve (e.g., sacral nerve). In some variations, the electrodes may be equally spaced apart from one another, while in other variations, spacing between the electrodes may vary. In some instances, the center-to-center distance between the electrodes may be from about 0.3 cm to about 1 cm, from about 0.5 cm to about 0.8 cm, and for example, about 0.6 cm. The implantable signal delivery device 1100A, 1100B may comprise a core 1106A, 1106B comprising electrically conductive wires made from metal (e.g., stainless steel, platinum, gold, silver, iridium, nickel, cobalt), metal alloy, or conductive polymer, and the core 1106A, 1106B may be surrounded by an insulating layer or jacket 1108A, 1108B, made from, for example, polyurethane, parylene, or silicone. The elongated body 1102 may comprise a rounded distal tip 1110A, 1110B.

In some variations, the elongated body may further comprise one or more tines 1112A, 1112B (e.g., two, three, four, or more) along a length of the elongated body 1102A, 1102B. The tines 1112A, 1112B may comprise a single or a plurality of elongate elements or rods (e.g. two, three, four, or more). The tines 1112A, 1112B may be made from an insulating material (e.g., polyurethane, polytetrafluoroethylene, parylene, or silicone) and may be used to anchor or otherwise couple the implantable signal delivery device 1100A, 1100B in or to a patient's tissue (such as muscle tissue) and to limit or otherwise prevent it from detrimentally moving (e.g., swaying, back-and-forth laterally or otherwise). The tines 1112A, 1112B may extend outward from the elongate body 1102A, 1102B at an extension angle $\theta_A$, $\theta_B$ In some variations, the extension angle $\theta_A$, $\theta_B$ for one or more of the tines 1112A, 1112B (e.g., one, two, three, four, five, six, seven, eight, all the tines) may be an acute angle (e.g., from about 5° to about 45°, including all values and sub-ranges therein). In some variations, each of the tines 1112A, 1112B may extend at the same extension angle $\theta_A$, $\theta_B$, while in other variations, the extension angle $\theta_A$, $\theta_B$ may vary between the tines 1112A, 1112B. In some variations, each of the tines 1112A, 1112B positioned at the same or similar positions along the length of the elongate body 1102A, 1102B may extend at the same extension angle $\theta_A$, $\theta_B$. In some variations, all of the tines 1112A, 1112B may extend outward in the same general direction, while in other variations, a first portion of the tines 1112A, 1112B may extend in a first direction, and a second portion of the tines 1112A, 1112B may extend in a second, different direction. For example, in some variations, all of the tines 1112A may be angled toward a proximal end of the elongate body 1102A (as depicted in FIG. 11A) or a distal end of the elongate body. In some variations, all of the tines 1112A may be parallel to one another. In other variations, a first portion of the tines (e.g., one, two, three, four, five, six, or more) may be angled toward a proximal end of the elongate body 1102B and a second portion of the tines (one, two, three, four, five, six or more) may be angled toward a distal end of the elongate body 1102B (as depicted in FIG. 11B). In some instances, it may be beneficial to utilize an implantable signal delivery device comprising tines extending in different directions (e.g., toward the proximal and distal ends of the devices) to assist in anchoring the implantable signal delivery device in the tissue (e.g., muscle) and to limit or prevent detrimental movement of the device (e.g., back-and-forth movement). In some variations, the tines 1112A, 1112B may be positioned proximally of the stimulation electrodes 1104A, 1104B. For example, in some instances, the distal-most tine 1112A, 1112B may be from about 5 mm to about 30 mm from the proximal-most stimulation electrode 1104A, 1104B.

Turning back to FIG. 1, in some instances, the stimulation electrode 103 may comprise a shape that conforms to a patient's tissue. For example, in one variation, the metallic stimulation electrode 103 may be polymer-coated, and the metallic polymer-coated stimulation electrode 103 may be formed from curable liquid pre-polymer after injection at a desired location in the patient, such that the polymer may conform to a shape of a portion of the patient's body, for example, the sacral nerve and/or the sacral foramen, and may create a solid conductive polymer after curing.

As mentioned above, the implantable signal delivery device 102 may be coupled to the pulse generator 101 via a wired or a wireless link. In variations in which the implantable signal delivery device 102 and the pulse generator 101 coupled using a wired connection, the proximal end of the implantable signal delivery device 102 may comprise a single or a plurality of contacts (e.g. 2, 3, 4, or more), which may be configured to electrically couple with corresponding contacts on the pulse generator 101. In variations in which the implantable signal delivery device 102 is wirelessly coupled to the pulse generator 101 (e.g., an implantable or an external pulse generator), the proximal end of the implantable signal delivery device 102 may comprise an inductively powered antenna configured to receive information about stimulation parameters from the pulse generator 101. Information about stimulation parameters may be sent using a frequency modulator, an amplitude modulator, and/or other suitable circuitry for modulating inductive protocols.

The temporary signal delivery device 117 may comprise an elongated body and a stimulation electrode 119. In some variations, the elongated body may comprise a distal tip made from an electrically conductive material (such as metal, metal alloy, or conductive polymer) that may act as the stimulation electrode 119. Thus, in some variations, the elongated body and the stimulation electrode 119 may be integrally formed. In other variations, a separate stimulation electrode may be coupled to the elongated body. The stimulation electrode 119 may be configured to apply a stimulation signal (e.g., a screening stimulation signal) to a nerve (e.g., sacral nerve). The distal tip of the elongated body may be pointed or rounded, and may be plated with metal (e.g., stainless steel, platinum, gold, iridium, silver), metal alloy or conductive polymer. The temporary signal delivery device 102 may comprise a core comprising electrically conductive wires made from a metal (e.g., stainless steel, platinum, silver, iridium, nickel, cobalt), metal alloy, or conductive polymer, which may be at least partially surrounded by an insulating layer or jacket, made from, for example, polyurethane, parylene, or silicone. In some variations, the entire portion of the elongated body between the pointed distal tip and the proximal end may be surrounded by an insulating layer, while in other variations, only a portion (e.g., 50%, 60%, 70%, between 50-70%, or the like) of the elongated body between the pointed distal tip and the proximal end may be surrounded. The insulating layer may minimize or prevent the transmission of electrical current to undesired locations within the body near the temporary signal delivery device 117, for example, tissue above the sacral foramen. A portion of the elongated body of the temporary signal delivery device 117 that is external to the patient's body (e.g., the proximal end) may be coupled to an external pulse generator using, for example, a connector, an alligator clip, conductive tape, conductive gel, a combination thereof, or the like. In some variations, the temporary signal delivery device 117 may be an electroacupuncture needle.

Sensors

Referring back to FIG. 1, the system 100 may comprise a wearable and/or implantable sensor 115 configured to collect data (e.g., cardiac data, disease activity data, bodily activity data) and send the data to the pulse generator. The sensor 115 may be operably coupled to the pulse generator 101, via, for example, a wired or wireless link. For example, as depicted in FIG. 1, the sensor 115 may be coupled to the pulse generator via a sensor lead 116. In other variations, the sensor 115 may be positioned separately and remotely from the pulse generator 101 and may be wirelessly coupled to the pulse generator 101. In some variations, the sensor 115 may be wirelessly coupled to the pulse generator 101 using an Ultra High Frequency (UHF) band (e.g., Bluetooth, BLE, Wi-Fi, and ANT+ protocols operating at 2.4-2.5 GHz band), Super High Frequency (SHF) band (e.g., Wi-Fi protocols operating at 3.6-3.7 GHz and 5.1-6.0 GHz bands), and/or a Very High Frequency (VHF) band. While depicted in FIG. 1 as comprising a single sensor 115, it should be appreciated that the system 100 may comprise a plurality of sensors 115 (e.g., two, three, four, five, six or more), and the number of sensors 115 utilized may be determined based on a variety of factors, including but not limited to, patient condition, patient diagnosis, and/or clinician preference.

In some variations, the sensor 115 may be an autonomic nervous system sensor (e.g., a cardiac sensor), a disease activity sensor (e.g. an inflammatory disease activity sensor or an oxidative stress disease activity sensor), or a bodily activity sensor (e.g. a metabolic activity sensor, a respiratory activity sensor, a gastrointestinal activity sensor or a circadian rhythm sensor). The autonomic nervous system sensor may be a sensor configured to measure autonomic nervous system data from which one or more autonomic nervous system parameters may be calculated or extracted, the disease activity sensor may be a sensor configured to measure disease activity data from which one or more disease activity parameters may be calculated or extracted, and the bodily activity sensor may be a sensor that measures bodily activity data from which one or more bodily activity parameters may be calculated or extracted. In some embodiments, the system 100 may comprise all of, or any combination of, the aforementioned sensors. For example, in some variations, the system may comprise at least one autonomic nervous system sensor and at least one disease activity sensor. In other variations, the system may comprise at least one autonomic nervous system sensor and at least one bodily activity sensor. Additionally, while the autonomic nervous system sensor, disease activity sensor, and bodily activity sensors are described above as separate sensors, in some various, a single sensor may serve as one or more of an autonomic nervous system sensor, a disease activity sensor, and a bodily activity sensor (e.g., both a disease activity sensor and a bodily activity sensor).

For example, in some variations, the system may comprise a single sensor, and the data measured with the single sensor may be used to determine a plurality of physiological parameters from different parameter groups (e.g., an autonomic nervous system activity parameter and a disease activity parameter, a disease activity parameter and a bodily activity parameter, an autonomic nervous system activity parameter and a bodily activity parameter). For example, in some of these variations, the system may comprise a single implanted core body temperature sensor, and the core body temperature data may be used to determine both a disease activity parameter and a bodily activity parameter. In particular, in this variation, the core body temperature data may be averaged over a relatively short duration (e.g., 30 minutes, 45 minutes, one hour, two hours) and over a longer duration (4 hours, 5 hours, 6 hours, 7 hours, 8 hours, 9 hours, or more), and the short duration average may be used to determine a bodily activity parameter (e.g., amplitude of metabolic activity) and the long duration average may be used to determine a disease activity parameter (e.g., amplitude of inflammatory disease activity). The bodily activity parameter and the disease activity parameter may then be used to determine a disease state and/or a physiological state (e.g. "flare" and "food consumption").

In other variations, the system may comprise a plurality of sensors (e.g., two, three, four, or more). In these variations, the data from each sensor may be used to determine physiological parameters from different parameter groups or a single sensor may be used to determine physiological parameters from two different parameter groups and a third sensor may be used to determine physiological parameters from a third parameter group. For example, the system may comprise a first sensor and a second sensor, and the data from the first sensor may be used to determine one or more disease activity parameters and the data from the second sensor may be used to determine one or more autonomic nervous system parameters or one or more bodily activity parameters. In another example, the system may comprise a first sensor, a second sensor, and a third sensor, and the data from the first sensor may be used to determine one or more disease activity parameters, the data from the second sensor may be used to determine one or more autonomic nervous system parameters, and the data from the third sensor may be used to determine one or more bodily activity parameters. In another embodiment, the system may comprise a first sensor and a second sensor, and the first sensor may be used to determine one or more disease activity parameters and one or more bodily activity parameters, and the second sensor may be used to determine one or more autonomic nervous system parameters.

In some variations, the sensor 115 may comprise at least one of an implanted electrocardiographic electrode, implanted core body temperature sensor, implanted oxygenation sensor, implanted electromyographic electrode, implanted movement sensor, implanted non-enzymatic electrochemical sensor, and/or external diagnostic device (e.g., wearable device) configured to measure values of heart rate, inflammatory disease activity, oxidative stress disease activity, metabolic activity, respiratory activity, gastrointestinal activity, and/or circadian rhythm from patient's tissue, blood, skin, saliva, breath, urine, stool (feces), sweat (perspiration), and/or tears. The implanted oxygenation sensor may detect blood oxygenation level, oxygen saturation level, oxygen consumption, and/or oxygen pressure. The implanted electromyographic electrode and implanted movement sensor may detect movement of arterial blood, heart, chest wall, diaphragm, stomach, small intestines, large intestines, bladder, kidney, and/or liver. The implanted non-enzymatic electrochemical sensor may utilize amperometry, cyclic voltammetry, and/or fast scan cyclic voltammetry sensors and may detect pH, cations (e.g. sodium, potassium, calcium, magnesium), anions (e.g. chloride, chlorate, perchlorate, phosphate, acetate, nitrite, nitrate, sulfite, sulfate, thiosulfate, carbonate, bicarbonate, ascorbate, iodide, lactate), norepinephrine, adenosine, dopamine, glucose, lactose, charged proteins, bacteria, and/or oxygen. The external diagnostic device may detect electrical signal, optical signal, electrochemical signal, absorption spectroscopy signal, Raman spectroscopy signal, gas chromatography-mass spectrometry signal, high performance liquid chromatography-mass spectrometry signal, and/or selected-ion flow-tube mass spectrometry signal. In some variations, a single sensor may be used to measure multiple signals of the autonomic nervous system activity, disease activity, and/or bodily activity. For example, in some of these variations, a single core body temperature sensor may be used to measure both the inflammatory disease activity and food consumption activity. In other variations, separate sensors may be used to measure autonomic nervous system activity, disease activity, and bodily activity. For example, a cardiac sensor may be used to measure electrocardiographic activity and a core body temperature sensor may be used to measure an inflammatory disease activity.

Examples of autonomic nervous system sensors (cardiac sensors) include but are not limited to: implanted electrocardiographic electrodes, wearable (e.g., wrist-worn) electrocardiographic and photoplethysmographic electrodes, and external diagnostic devices configured to measure values of heart rate.

Examples of inflammatory disease activity sensors include but are not limited to: implanted core body temperature sensors, implanted electromyographic electrodes, implanted movement sensors, implanted non-enzymatic electrochemical sensors, and external diagnostic devices configured to measure values of inflammatory disease activity from a patient's tissue, blood, skin, saliva, breath, urine, stool (feces), sweat (perspiration), and/or tears.

Examples of oxidative stress disease activity sensors include but are not limited to: implanted oxygenation sensors, implanted non-enzymatic electrochemical sensors, and external diagnostic devices configured to measure values of oxidative stress disease activity from patient's tissue, blood, skin, saliva, breath, urine, stool (feces), sweat (perspiration), and/or tears.

Examples of respiratory activity sensors include but are not limited to: implanted core body temperature sensors, implanted oxygenation sensors, implanted electromyographic electrodes, implanted movement sensors, implanted non-enzymatic electrochemical sensors, and external diagnostic devices configured to measure values of respiratory activity from patient's skin or breath.

Examples of metabolic activity sensors include but are not limited to: implanted core body temperature sensors, implanted oxygenation sensors, implanted electromyographic electrodes, implanted movement sensors, implanted non-enzymatic electrochemical sensors, and external diagnostic devices configured to measure values of metabolic activity from patient's tissue, blood, skin, saliva, breath, urine, stool (feces), sweat (perspiration), and/or tears.

Examples of gastrointestinal activity sensors include but are not limited to: implanted core body temperature sensors, implanted oxygenation sensors, implanted electromyographic electrodes, implanted movement sensors, implanted non-enzymatic electrochemical sensors, and external diagnostic devices configured to measure values of gastrointestinal activity from patient's tissue, blood, skin, saliva, breath, urine, stool (feces), sweat (perspiration), and/or tears.

Examples of circadian rhythm activity sensors include but are not limited to: implanted core body temperature sensors, implanted oxygenation sensors, implanted electromyographic electrodes, implanted movement sensors, implanted non-enzymatic electrochemical sensors, and external diagnostic devices configured to measure values of circadian rhythm from patient's tissue, blood, skin, saliva, breath, urine, stool (feces), sweat (perspiration), and/or tears.

As mentioned above, in some variations, the systems described here may comprise a plurality of sensors, for example, an autonomic nervous system sensor (e.g. electrocardiographic or photoplethysmographic electrode), a disease activity sensor (e.g. an inflammatory disease activity sensor or an oxidative stress disease activity sensor), and a bodily activity sensor (e.g. a metabolic activity sensor, a respiratory activity sensor, a gastrointestinal activity sensor or a circadian rhythm sensor). In some instances, it may be beneficial to utilize both an autonomic nervous system sensor and a disease activity sensor to inform adjustment of one or more of the stimulation parameters, as use of both data sets may allow for a more accurate determination of an autonomic nervous system state, physiological state, and/or disease state of a patient. More accurate determination of a patient's autonomic nervous system states, physiological states, and disease states may result in a reduction of unwanted side effects and an improvement of therapy efficacy.

More specifically, the use of two or more sensors may assist in calculating physiological parameters, for example, when patient has disorders or diseases other than gastrointestinal or unrelated health conditions. For example, in a variation in which the patient has two or more types of inflammation, using two or more sensors and thus, a two or more different data types (e.g., disease activity data and bodily activity data; disease activity data and autonomic activity data, or autonomic activity data, disease activity data, and bodily activity data), may assist in distinguishing between the types of inflammation. In one example, a patient may suffer from gastrointestinal inflammatory disease and may have a first type of inflammation that is attributable to the gastrointestinal disorder. The patient may also have a secondary type of inflammation that is unrelated to the gastrointestinal inflammatory disease. In some instances, it may be difficult to distinguish the two types of inflammation from the disease activity data measured using the disease activity sensor (e.g., a core body temperature sensor). In this circumstance, it may be beneficial to utilize a bodily activity sensor (e.g., an implanted non-enzymatic electrochemical sensor or an external diagnostic device), the data from which may assist in distinguishing between two types of inflammation.

External Programmer

The system 100 may also comprise an external programmer 104 that may be configured to communicate with and/or control the pulse generator 101. As shown in FIG. 1, the external programmer 104 may comprise a housing 105 carrying multiple input devices 106 (e.g., push buttons, track wheels, directional keys, etc.), a display 107 (e.g., a liquid crystal display). The external programmer 104 may also comprise internal circuitry (not shown) that may be configured to create a bidirectional wireless data link 109 to communicate with the pulse generator 101 and to adjust its operation (e.g., by changing a stimulation program and/or one or more stimulation parameters). In certain embodiments, the external programmer 104 may be configured as a handheld device. In other embodiments, components of the external programmer 104 may have other portable configurations. For example, the external programmer 104 or components thereof may be mounted on a band, strap, or belt, that maybe worn around a patient's wrist, arm, hand, finger, head, forehead, neck, ankle, torso, chest, or waist. In some instances, the external programmer 104 or components thereof may be mounted to attach to a patient's clothing (e.g., via a clip, pin, or the like), may be shaped like earphones or glasses such that they may be worn in a patient's ears or on a patient's face, or may be incorporated within a handheld computing device (such as a laptop computer, a notebook computer, a tablet computer, a PDA, a smart phone, or a smart watch). In some variations, the external programmer 104 may be omitted and a computer may establish a bidirectional wireless data link to communicate with the pulse generator 101.

Charging Antenna

In some instances, the system 100 may also comprise a wireless charging antenna 108, which may electrically couple to the pulse generator 101 via a wireless power communication link 114 to charge the battery 128 of the pulse generator 101. In some variations, the wireless charging antenna 108 may comprise an induction coil.

Computer

In some embodiments, the therapy system 100 may also comprise a computer 110. The computer 110 may be coupled to the external programmer 104 via a bidirectional wireless data link 111 (e.g., a Wi-Fi link, a Bluetooth link, an NFC link, etc.). In some variations, the computer 110 may be coupled to a cloud server 113 via a bidirectional network connection 112 (e.g., an Internet connection, an intranet connection, or the like). In some instances, the computer 110 and/or the cloud server 113 may be omitted. It should be appreciated that the systems described herein may also comprise other suitable network components, for example, routers, switches, data storage centers, or the like.

The computer 110 may comprise one or more processors, tangible memories (e.g., random access memories (RAMs), read-only memories (ROMs), and/or programmable read only memories (PROMS)), tangible storage devices (e.g., hard disk drives, CD/DVD drives, and/or flash memories), system buses, video processing components, network communication components, input/output ports, and/or user interface devices (e.g., keyboards, pointing devices, displays, microphones, sound reproduction systems, and/or touch screens).

The computer 110 may be a desktop computer or a portable computer, such as a laptop computer, a notebook computer, a tablet computer, a PDA, a smart phone, a smart watch, or part of a larger system, such a vehicle, appliance, and/or telephone system.

The computer 110 may comprise software (e.g., one or more operating systems, device drivers, application programs, and/or communication programs). In some variations, the software may comprise programming instructions and may include associated data and libraries. When included, the programming instructions may be configured to implement one or more algorithms that implement one or more of the functions of the computer system, as recited herein. The description of each function that is performed by each computer system also constitutes a description of the algorithm(s) that performs that function.

The software may be stored on or in one or more non-transitory, tangible storage devices, such as one or more hard disk drives, CDs, DVDs, and/or flash memories. The software may be in source code and/or object code format. Associated data may be stored in any type of volatile and/or non-volatile memory. The software may be loaded into a non-transitory memory and executed by one or more processors.

Methods

Described here are also methods for treating one or more chronic gastrointestinal disorders (such as irritable bowel syndrome, inflammatory bowel disease, ulcerative colitis, ulcerative proctitis, Crohn's disease, chronic constipation, chronic fecal incontinence, functional abdominal pain, gastroesophageal reflux disease, esophageal dysmotility, pseudo-obstruction, functional dyspepsia, gastroparesis, intestinal dysmotility, celiac disease, anorexia, colonic inertia, pancreatitis), chronic auto-immune diseases (such as autoimmune thyroid disease, ankylosing spondylitis, multiple sclerosis, myasthenia gravis, psoriasis, rheumatoid arthritis, Sjögren's syndrome, systemic lupus erythematosus, systemic sclerosis, juvenile idiopathic arthritis, Still's disease, macrophage activation syndrome, cytokine release syndrome, cytokine storm syndrome, hyperinflammation, acute respiratory distress syndrome, hemophagocytic lymphohistiocytosis, pneumonitis, chronic obstructive pulmonary disease, asthma, myocarditis), and metabolic disorders (such as type 2 diabetes mellitus, obesity, dyslipidemia, cardiometabolic disease, non-alcoholic fatty liver disease, chronic kidney disease, polycystic ovary syndrome, hypertension) by providing electrical stimulation therapy to a target peripheral nerve, for example, the sacral nerve. In some variations, electrical stimulation therapy may be delivered to specific sacral nerves, such as: S1, S2, or S3, either unilaterally or bilaterally. In other variations, electrical stimulation therapy may be delivered to the nerves formed distally from the sacral nerves, such as: the superior gluteal nerve, the inferior gluteal nerve, the sciatic nerve, the tibial nerve, the common peroneal (common fibular) nerve, the posterior femoral cutaneous nerve, the pudendal nerve, the obturator internus nerve, the quadratus femoris nerve, or the piriformis nerve.

Methods for delivering a stimulation signal or stimulation program to a nerve of a patient may generally comprise receiving disease activity data from a disease activity sensor, determining a disease state of the patient based on the disease activity data, adjusting a nerve stimulation parameter of a stimulation signal based on the determined disease state, and applying an adjusted stimulation signal comprising the adjusted nerve stimulation parameter to the nerve of the patient to, for example, treat or otherwise decrease symptoms associated with a chronic gastrointestinal disorder. Methods may further comprise receiving autonomic nervous system activity data and/or bodily activity data, determining an autonomic nervous system state and/or a physiological state. In these variations, the nerve stimulation parameter may be adjusted based on a combination of the disease state and the autonomic nervous system state and/or the bodily activity state. In some variations, starting and/or stopping application of the stimulation may be based on the determined disease state, and the autonomic nervous system state and/or the bodily activity state may be used to modulate one or more stimulation parameters.

In some variations, methods may generally comprise measuring electrical activity of the heart using a cardiac sensor, measuring disease activity using one or more disease activity sensors, measuring bodily activity using one or more bodily activity sensors, extracting or calculating one or more physiological parameters from the data using, for example, the methods described herein, determining and/or recording an autonomic nervous system state, physiological state, and/or disease state of the patient using the physiological parameters, adjusting the value of a stimulation parameter of a stimulation signal, and instructing a signal delivery device to apply a stimulation signal comprising the adjusted stimulation parameter to, for example, treat or otherwise decrease symptoms associated with a chronic gastrointestinal disorder. In some variations, the methods may comprise automatically starting or stopping stimulation based at least in part on the determined autonomic nervous system state, physiological state, and/or disease state.

Methods may further comprise surgically implanting one or more components of the stimulation systems described here. For example, methods may comprise surgically implanting the implantable signal delivery device 102 and one or more of the pulse generator 101, sensor 115, and sensor lead 116. In variations in which the pulse generator 101 is implanted, surgically implanting the pulse generator 101 may comprise making a first skin incision above the gluteal muscle and placing the implantable pulse generator 101 through the first skin incision in a subcutaneous pocket in the lower back region. Implanting the implantable signal delivery device 102 may comprise making an incision (using, for example, a needle or a scalpel and tissue-dissecting surgical tools) in the area about 2 centimeters lateral from the median sacral crest and inserting the implantable signal delivery device 102 through the second incision into a sacral foramen. In some variations, the implantable signal delivery device 102 may be advanced toward and placed into the sacral foramen S1, S2, and/or S3, either unilaterally or bilaterally. In some variations, the implantable signal delivery device 102 may be inserted using a needle or a scalpel, and tissue-dissecting surgical tools. In variations in which a needle is used, additional tools, for example, a directional guide, stylet, dilator, introducer, and/or other accessory insertion tools that may be fitted inside the needle, may also be utilized.

Figure 12A:
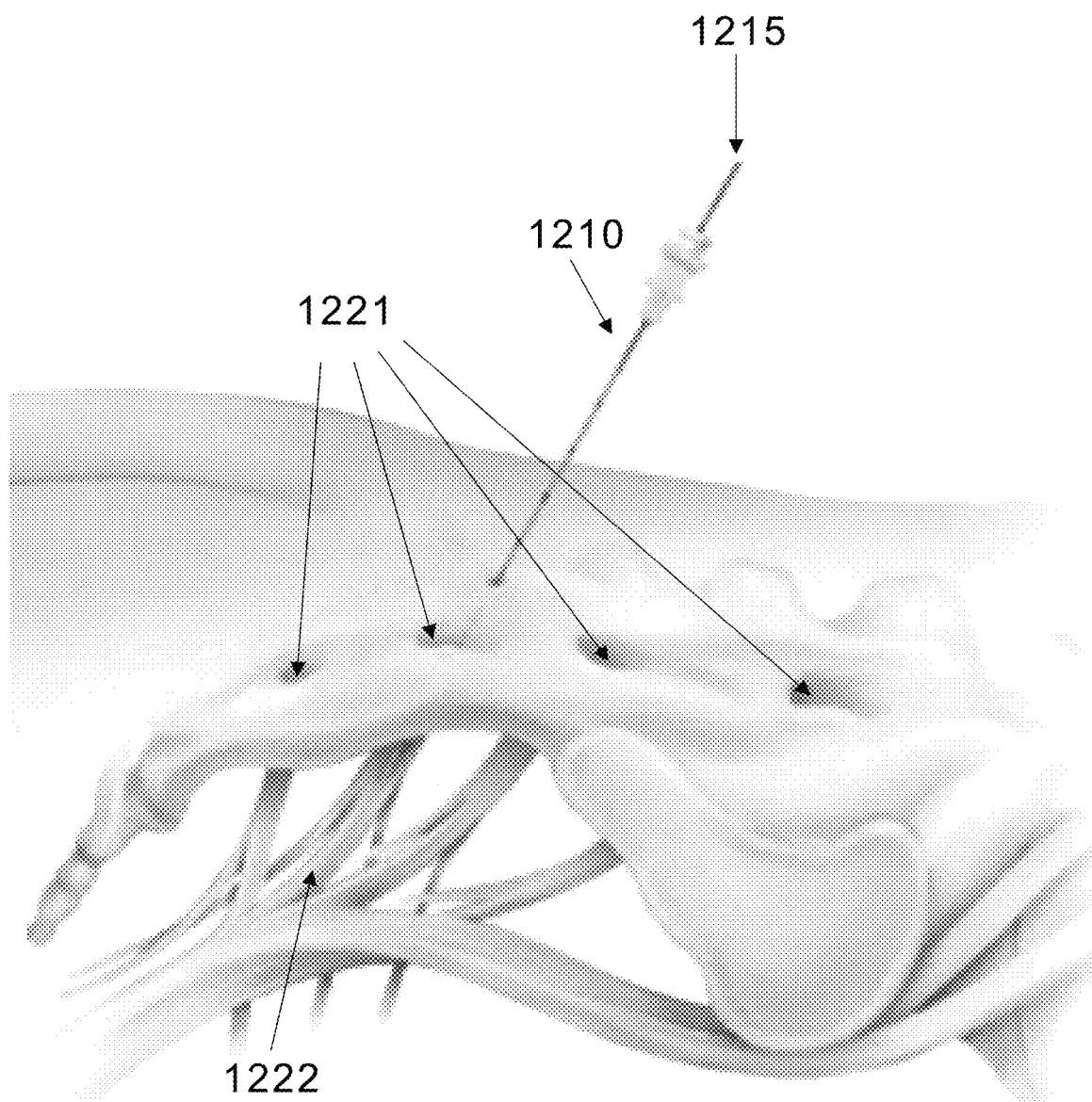
FIGS. 12A, 12B, and 12C depict a method for implanting a signal delivery device into a sacral foramen.
Figure 12B:
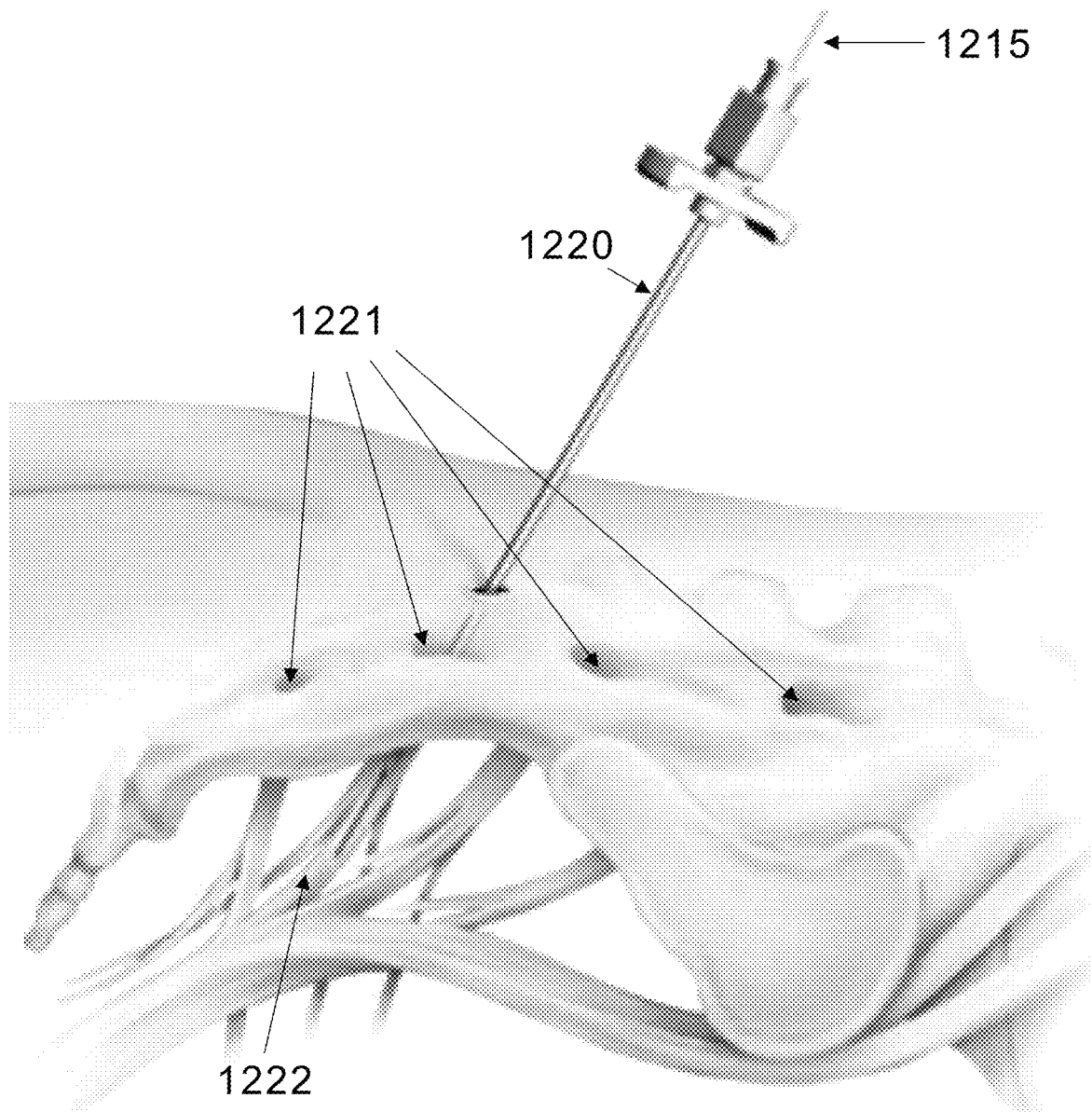
Figure 12C:
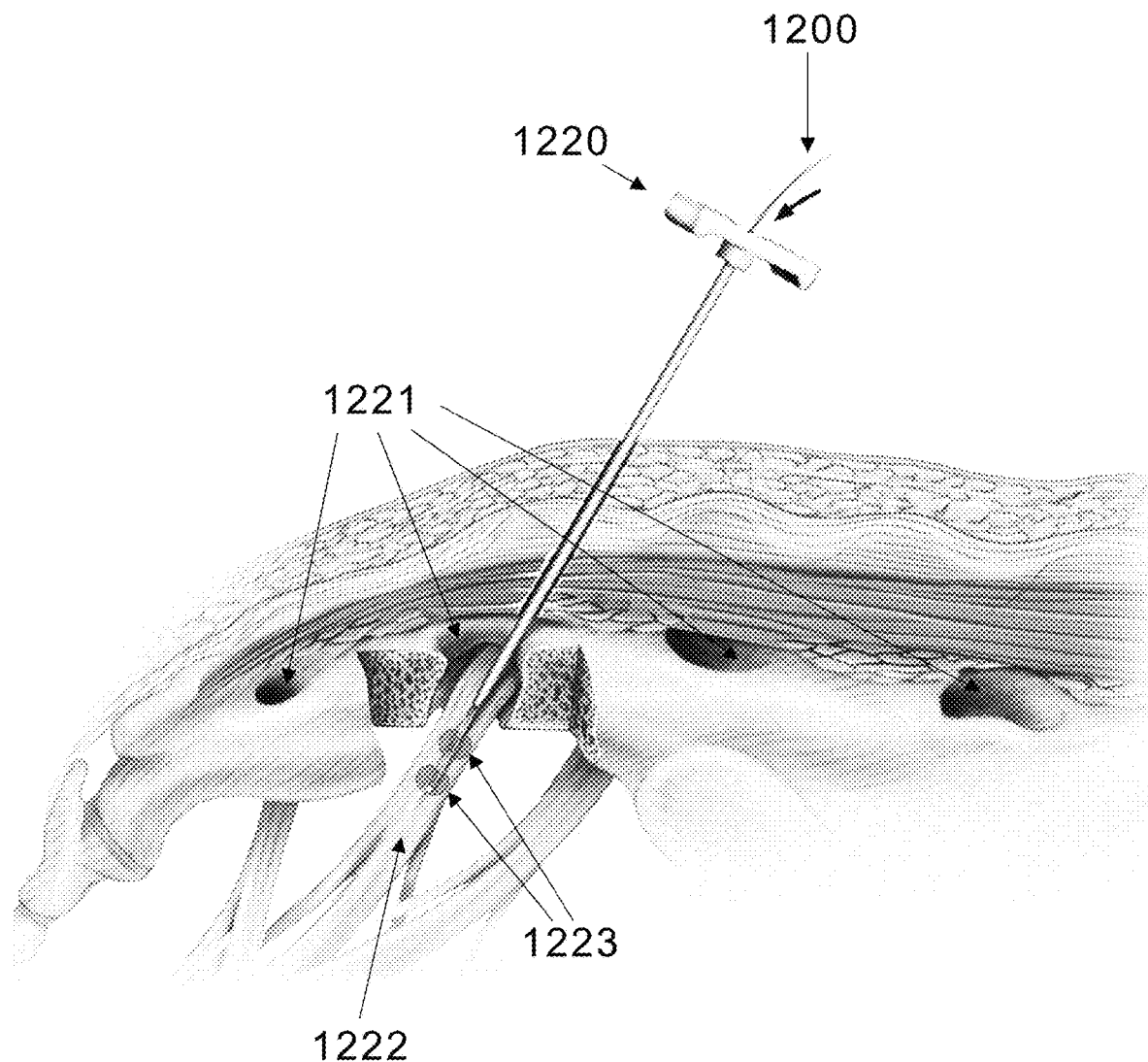

In some variations, the stimulation electrode 103 of the implantable signal delivery device 102 may comprise one or more metallic stimulation electrodes, which may optionally be used with a polymer (e.g., may be polymer-coated). FIGS. 12A, 12B, and 12C depict a method for implanting a signal delivery device into a sacral foramen. As depicted in FIG. 12A, during the implantation procedure, a tubular member 1210, such as a needle, may be inserted through a patient's skin into the sacral foramen 1221. A directional guide 1215 (e.g., a guidewire) may be advanced through a lumen of the tubular member 1210 and into the sacral foramen 1221. While holding the directional guide 1215 in place, the tubular member 1210 may be then retracted or otherwise removed from the patient's body.

As depicted in FIG. 12B, an introducer 1220 may then be advanced over the directional guide 1215 and into the sacral foramen 1221, after which the directional guide may be retracted or otherwise removed, leaving the introducer 1220 in place.

In some variations, a pre-polymer delivery device may then be advanced through a lumen of the introducer 1220 such that the distal end of the pre-polymer delivery device is positioned within a patient's sacral foramen. Once appropriately positioned within the sacral foramen 1221, in variations utilizing a metallic polymer-coated electrode, one or more (e.g., two, three, four, or more) polymer boluses 1223 may be injected and/or directed toward and/or around the sacral nerve 1222 through the lumen of the pre-polymer delivery device. In some variations, a syringe may be used to inject the pre-polymer through the pre-polymer delivery device and into a patient's sacral foramen. In these variations, methods may further comprise filling a syringe with liquid pre-polymer, coupling the syringe to the pre-polymer delivery device, and advancing a plunger of the syringe to gradually inject liquid pre-polymer into the sacral foramen to fill the space around the sacral nerve. In some variations, filling the syringe may comprise filling a dual-chambered syringe with a 2-part pre-polymer mix. After delivery of one or more polymer boluses, the pre-polymer delivery device may then be withdrawn.

The implantable signal delivery device 1200 may be advanced through a lumen of the introducer 1220. In some variations, where a pre-polymer delivery device is used, the implantable signal delivery device 1200 may be positioned such that the stimulation electrodes (e.g., metallic stimulation electrodes) may be positioned within or may otherwise be in alignment with the individual polymer boluses 1223, as depicted in FIG. 12C.

A stylet (e.g., a curved stylet) may be advanced through a lumen of the implantable signal delivery device 1200. The stylet may assist in bending or otherwise moving the tip of the implantable signal delivery device 1200. In variations in which a curved stylet is used, the stylet may bend the distal end or a portion thereof of the implantable signal delivery device 1200 in accordance with the curvature of the stylet such that distal end or a portion thereof assumes a curvature matching that of the stylet. Once the stylet is fully inserted, it may additionally or alternatively be rotated to assist in positioning the distal end the implantable signal delivery device 1200 in close proximity to the sacral nerve (e.g., a particular branch of the sacral nerve).

In variations utilizing a pre-polymer delivery device, the pre-polymer delivery device may comprise any device suitable for delivery of a liquid pre-polymer to a particular anatomical location. For example, in some variations, the pre-polymer delivery device may comprise an elongate body with a lumen therethrough and a distal outlet in fluid communication with the lumen. In some variations, the distal outlet may be at the distal-most tip of the elongate body of the pre-polymer delivery device (i.e., the elongate body may have an open distal end), while in other variations, the distal outlet may traverse a sidewall of the elongate body. In some embodiments, the pre-polymer delivery device may be or may comprise a needle or a sheath (e.g., a plastic sheath).

In some variations, the liquid pre-polymer may be injected at a specific depth of the sacral foramen (e.g., a depth corresponding to the depth of the desired placement for a stimulation electrode) and/or may be delivered in a specific direction from the distal outlet of the pre-polymer delivery device (e.g. only toward anterior, posterior, left, or right side of the sacral foramen cavity). For example, the liquid pre-polymer may be injected at an injection depth of from about 3 cm to about 12 cm from a patient's skin surface, including all values and sub-ranges therebetween.

In some embodiments, the distal end of the pre-polymer delivery device may be advanced to a first location to deliver a first bolus of liquid pre-polymer and may be moved to one or more additional locations (e.g., a second location, a third location, etc.) to deliver additional boluses of liquid pre-polymer. In some variations, the first location may be the distal most or deepest location within the sacral foramen, and the distal end may be retracted to a second, shallower location to deliver a second bolus of liquid pre-polymer. The distal end of the pre-polymer delivery device may be retracted one or more times after initial insertion to the first location, and may deliver one or more additional boluses at each location. In some variations, the distal end of the pre-polymer delivery device may be retracted in increments corresponding to a center-to-center distance between adjacent metallic stimulation electrodes on the signal delivery device. For example, the distal end of the pre-polymer delivery device may be advanced to a first location at a first depth, a bolus of liquid pre-polymer may be delivered at the first location, the distal end of the pre-polymer delivery device may be retracted between about 0.5 cm and 0.8 cm (e.g., 0.6 cm) to a second location at a second depth, and a second bolus of liquid pre-polymer may be delivered at the second location.

In some variations, delivery of liquid pre-polymer as spatially separated boluses may allow the metallic polymer-coated electrodes to be electrically insulated from one another.

As mentioned above, the implantable signal delivery device 102 may be advanced through the lumen of the introducer and a distal end of the implantable signal delivery device may contact (e.g., electrically contact) the liquid pre-polymer. The liquid pre-polymer may cure in situ after a period of time (e.g., about 5 minutes, about 10 minutes, about 30 minutes, about 1 hour, about 1 hour to about 5 hours, about 1 hour t about 10 hours, about 1 hour to about 24 hours, about 5 minutes to about 24 hours) and may form a solid tissue-conforming compliant conductive polymer that conforms to a shape of the sacral nerve and/or a portion of the sacral foramen. Curing of liquid pre-polymer may involve polymerization and/or cross-linking of monomers and oligomers into the solid polymer.

In some variations, liquid pre-polymer may comprise a two-part silicone elastomer or hydrogel (e.g., polyvinyl alcohol, gelatin, collagen, starch, chitosan, albumin, polyglucosamine, polyethylene glycol, polyethylene glycol dimetacrylate, poly-glutamic acid, polyurethane, poly caprolactone, polyethylene oxide, or polyoxyethylene) mixed with metallic particles (e.g., platinum, iridium, gold, silver, nickel, cobalt, stainless steel). In some of these variations, the weight ratio of metallic particles to silicone or hydrogel may be about 20%, about 30%, about 40%, about 50%, about 60%, about 70%, about 80%, between about 20% and about 50%, or between about 20% and about 80%, and the metallic particles may comprise a spherical, spheroidal, granular (gravel-like), cylindrical shape, or a combination thereof. In some variations, the metallic particles may be 2-dimensional (e.g., in the form of a flake) or 1-dimensional (e.g., in the form of a fiber). In some variations, the stimulation electrode 103 may comprise both a metallic stimulation electrode (such as electrode 1104A, 1104B) and a curable conductive polymer electrode.

In some variations, after the signal delivery device is advanced to a position within the sacral foramen in which the metallic stimulation electrodes of the implantable signal delivery device are aligned and in contact with the individual polymer boluses, electrical current may be delivered to the polymer boluses for one or more of catalyzing curing of the liquid pre-polymer (e.g., speed up the curing process) and electrodeposition (electroplating). For example, electrical current may be delivered from the metallic stimulation electrodes on the implantable signal delivery device to the polymer boluses to catalyze the curing process and/or to facilitate electrodeposition, as will be described in more detail herein. In some variations, the same electrical current may be used to both catalyze curing and for electrodeposition, while in other variations, a first electrical current may be applied to catalyze curing, and a second electrical current may be applied for electrodeposition. In yet other variations, methods may comprise applying an electrical current that may be used to catalyze curing, but not for electrodeposition, or vice versa.

In some instances, utilizing an electrodeposition process may enhance the electrical connection between the metallic stimulation electrodes and the individual polymer boluses, while catalyzing curing of the liquid pre-polymer may reduce the cure time necessary to form a solid polymer electrode thereby reducing overall implantation procedure duration. As mentioned above, these processes may comprise passing electrical current through the metallic stimulation electrodes. For example, in some variations, electrical current may be passed between two of the metallic stimulation electrodes on the implantable signal delivery device, while in other variations, electrical current may be passed between a single metallic stimulation electrode on the implantable signal delivery device and a distant return electrode (e.g., a metallic IPG enclosure or a patch electrode applied to a patient's skin).

For electrical catalysis of the curing process and/or for methods utilizing electrodeposition, the electrical voltage may be in a range from −3V to +3V and may be applied for a period from 1 minute to 12 hours, either continuously or pulsed at a frequency from 10 Hz to 400 kHz. In some variations, application of the electrical voltage may allow for simultaneous electrical catalysis and electrodeposition (e.g., the same electrodes and voltage may be used for both processes simultaneously). The curing and/or electrodeposition processes may be considered completed when all liquid pre-polymer is cured and a solid polymer has formed In variations in which an implantable pulse generator is used, implantation of the implantable signal delivery device 102 may further comprise routing a proximal end of the implantable signal delivery device 102 from the second incision to the first incision and coupling the implantable signal delivery device 102 and the implantable pulse generator 101, by, for example, connecting contacts on the implantable signal delivery device 102 with corresponding contacts on the implantable pulse generator 101.

In variations in which one or more sensor 115 is also implanted, surgically implanting the sensor 115 may comprise making a third incision for inserting the sensor 115 with the sensor lead 116 into a subcutaneous or intramuscular location, and coupling the sensor 115 with the pulse generator, by, for example, connecting contacts on the sensor lead 116 with corresponding contacts on the implantable pulse generator 101. In some variations, it is unnecessary to make an additional incision to implant the sensor 115, and a prior incision (e.g., the first or the second incision) may be used instead.

Surgical implantation of the system components may be performed via open surgery or minimally-invasive surgery (e.g., endoscopic or laparoscopic surgery) under general or local anesthesia. A hospital stay may or may not be required.

In some variations, the methods described here may comprise a non-surgical screening phase, during which temporary nerve therapy may be delivered to a patient (e.g., a patient suffering from a chronic disorder, such as a chronic gastrointestinal disorder). The screening phase may occur before implantation of one or more system components (e.g., the implantable signal delivery device 102 and/or an implantable pulse generator) for treatment during a treatment phase using extended nerve stimulation therapy. In these variations, a temporary signal delivery device and external pulse generator may be utilized to assess the suitability of a patient for extended nerve stimulation therapy. A physician may perform one or more initial or baseline tests before delivering temporary therapy during the screening phase and may perform one or more of the same tests during and/or at the end of the screening phase to evaluate the efficacy of the temporary therapy. For example, a physician may preform one or more tests (e.g., Cardiovagal Test, Heart Rate Variability Test, Sympathetic Skin Response, Valsalva Maneuver, Tilt Table Test, Gastric Emptying Test, Quantitative Sudomotor Axon Reflex Test, Thermoregulatory Sweat Test, Urodynamic Test) to evaluate the autonomic nervous system function, administer one or more disease questionnaires (e.g., Inflammatory Bowel Disease Questionnaire, Mayo score) and/or one or more disease tests (e.g. esophageal manometry, gastroduodenal manometry, anorectal manometry, intestinal endoscopy, calprotein and blood in stool (feces), C-reactive protein in blood, Erythrocyte Sedimentation Rate) to evaluate the disease activity. The physician or care provider may perform the tests/provide the questionnaires before the temporary therapy and during, and/or after the temporary therapy. If it is determined, based on the results of the screening phase, that extended nerve stimulation therapy is likely to be efficacious for a patient, the patient may progress to the treatment phase, in which one or more system components may be surgically implanted as described above. However, if it is determined that extended nerve stimulation therapy is unlikely to be efficacious, or that the efficacy of the extended therapy is outweighed by the risks and/or cost associated with surgical implantation of one or more components of the system, the patient may not progress to the treatment phase and may therefore avoid the cost and health risks associated with the implantation surgery and extended therapy. The screening phase may be any length suitable to determine appropriateness of extended nerve stimulation therapy and may be, for example, between about 3 days and about 60 days (e.g., 14 days).

As mentioned above, during the screening phase, the temporary signal delivery device 117 may be utilized to deliver electrical stimulation (e.g., a screening stimulation signal) to a nerve (e.g., sacral nerve). Methods of placing the temporary signal delivery device may comprise inserting a distal end of the temporary signal delivery device through the skin of a patient (i.e., transcutaneously) and advancing the distal end toward and into a sacral foramen S1, S2 and/or S3, either unilaterally or bilaterally. The non-surgical transcutaneous insertion may be performed under no anesthesia or local anesthesia, and a hospital stay may not be required. Once the temporary signal delivery device has been inserted, accurate placement of the device may be confirmed, by, for example, applying electrical stimulation at a level above the threshold for activation of either the sensing fibers in the sacral nerve (originating from pelvic organs, legs, or other organs) or the motor fibers in the sacral nerve resulting in detectable twitching or movement of the pelvic of leg muscles.

The temporary signal delivery device may be left inserted and connected to an external pulse generator for the length of the screening phase. For example, in some variations, a temporary signal delivery device may be used for between about one hour and 21 days (e.g., 8 hours), after which it may be removed and later replaced with another temporary signal delivery device. In some embodiments, the temporary signal delivery device 117 may be removed after each stimulation session during the screening phase and a new temporary signal device 117 may be inserted at the next stimulation session. The stimulation applied using the temporary signal delivery device may be applied continuously or intermittently (e.g. for an ON period of about 0.1 hours to about 8 hours and an OFF period of about 16 hours to just below 24 hours (e.g., 23.9 hours, from about 23.5 hours to about 23.9 hours). For example, in some variations, the ON period may be about 1 hour, about 2 hours, about 3 hours, about 4 hours, from about 1 hour to about 2 hours, from about 1 hour to about 4 hours, or from about 2 hours to about 4 hours. The temporary stimulation may be delivered at a stimulation amplitude below the threshold for activation of the sensory and motor fibers in a nerve (e.g. 90% of the threshold), at a pulse width of about 100 microseconds to about 2 milliseconds (e.g. about 500 microseconds), at a frequency of about 1 to about 100 Hz (e.g. about 5 Hz), and at a duty cycle of about 5% to about 50% (e.g. about 10% with 10 sec of train duration and 90 sec of inter-train duration). One or more of the stimulation parameters of the stimulation delivered using the temporary signal delivery device during the screening phase (e.g., a screening stimulation) may be the same as, or different from, one or more of the stimulation parameters of the stimulation delivered during the treatment phase.

Figure 4:
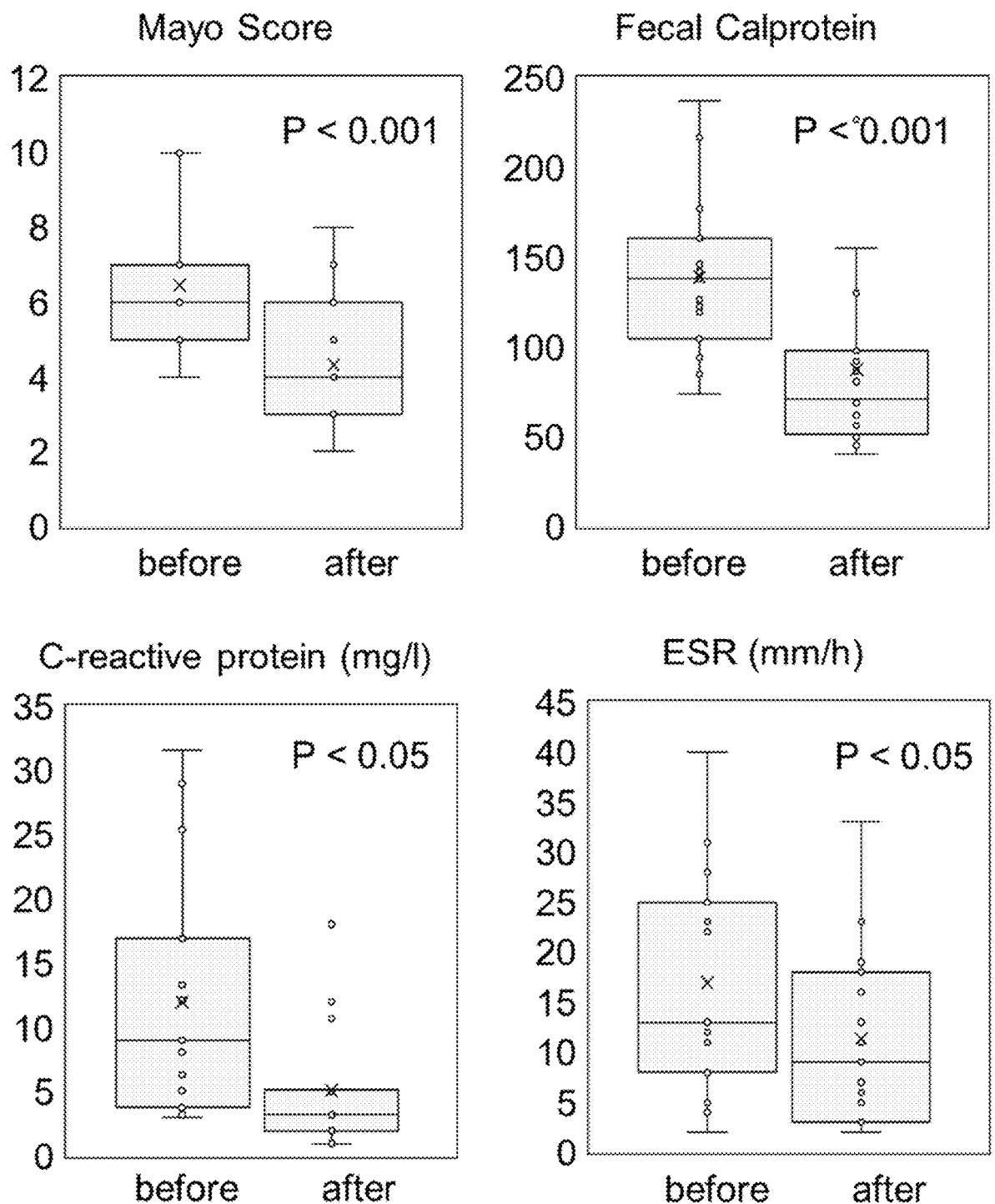
FIG. 4 illustrates the results of a non-surgical screening phase of the methods described here.

FIG. 4 illustrates the results of temporary sacral nerve stimulation therapy during a 14-day screening phase in 15 patients with moderate or severe ulcerative colitis. The temporary signal delivery devices, here the electroacupuncture needles, were inserted daily through the skin and advanced into S2 sacral foramen bilaterally for applying electrical stimulation to the sacral nerve. To evaluate the efficacy of the temporary therapy, blood and stool (fecal) tests were performed before and after the temporary therapy and various blood and stool parameters were evaluated, such as those related to the autonomic nervous system activity, disease activity, and pro-inflammatory and anti-inflammatory cytokines. Initial or baseline measurements to evaluate autonomic nervous system activity and disease activity were performed before and after the temporary therapy to evaluate the efficacy of the therapy. FIG. 4 depicts the results of measurements for four ulcerative colitis symptom tests in 15 patients: (left top) the Mayo score—an FDA-accepted Disease Activity Index for ulcerative colitis, (right top) calprotein in stool (feces), (left bottom) C-reactive protein in blood, (right bottom) Erythrocyte Sedimentation Rate (ESR) in blood. In the example depicted in FIG. 4, the Mayo score, fecal calprotein, C-reactive protein, and Erythrocyte Sedimentation Rate measurements all decreased from the timepoint before the therapy to the timepoint 14 days after temporary sacral nerve stimulation therapy, indicating a significant effect of the temporary sacral nerve stimulation therapy. The results of the non-surgical screening phase depicted in FIG. 4 indicate that all 15 patients with ulcerative colitis would be suitable candidates for the extended therapy.

After a patient progresses to the treatment phase (in variations in which a screening phase is utilized), initial setup of the extended system may begin. Initial setup of the extended system may begin before, during, or after implantation using an external programmer 104. In some variations, initial setup may occur soon after implantation. During the initial setup, a clinician or device representative may set the initial stimulation parameters, the initial correlation weights between the physiological parameters and the autonomic nervous system states, physiological states, and/or disease states, and the initial correlation weights between the autonomic nervous system states, physiological states, and/or disease states and the stimulation parameters for the algorithm. For example, an initial correlation weight may comprise a weight between the first amplitude and a first physiological state (e.g., "during light meal") and a weight between a second amplitude and a second physiological state (e.g., "during heavy meal"). Additionally or alternatively, an initial correlation weight may comprise a weight between the first amplitude and a first disease state (e.g., "early inflammatory response") and a weight between a second amplitude and a second disease state (e.g., "late inflammatory response"). In some variations, stimulation parameters may be initially set by the clinician with the patient's feedback. This may occur while the algorithm is in the learning phase. As mentioned above, during the automatic operation phase, the pulse generator 101 may automatically determine the autonomic nervous system state, physiological state, and/or disease state and the stimulation parameters.

During the learning phase, the weights may be adjusted based on feedback from a clinician or a patient, who may be periodically entering the stimulation parameters and autonomic nervous system states, physiological states, and/or disease states within the preset values selected at or shortly after implantation using an external programmer 104. The clinician, the device company representative, and/or other member of authorized personnel may also set a confidence level to indicate the end of the learning phase for the algorithm for example, from about 80% to about 99%. Once the pulse generator has collected sufficient data to meet the set confidence levels for setting the correlation weights, the pulse generator may automatically enter the automatic operation phase. In the automatic operation phase the pulse generator may automatically determine a patient's autonomic nervous system state, physiological state, and/or disease state, and may automatically adjust the stimulation parameters for the implantable signal delivery device 102 in response to a change in the physiological parameters (autonomic nervous system parameters, disease activity parameters, and bodily activity parameters). This may result in an improvement and/or maintenance of treatment efficacy, without further input from the patient.

During the learning phase, the pulse generator 101 may continuously or intermittently monitor the sensor data from the sensor 115 and the stimulation parameters from the external programmer 104, extract and/or calculate the physiological parameters (autonomic nervous system parameters, disease activity parameters, and bodily activity parameters) and/or adjust the stimulation parameters. In certain embodiments, the pulse generator 101 may detect a change in at least one stimulation program or a stimulation parameter (e.g., an amplitude and/or a frequency of stimulation). For example, the patient may increase or decrease the amplitude of the applied therapy signals using the external programmer 104, and the pulse generator 101 may record the amplitude adjustment and send the adjusted stimulation pulses to the implantable signal delivery device 102 or temporary signal delivery device 117.

When the pulse generator 101 detects a change in the sensor data or the physiological parameters, the pulse generator 101 may calculate all or a subset of the current physiological parameters (e.g. autonomic nervous system parameters, disease activity parameters, and bodily activity parameters). In certain embodiments, the physiological parameters may be calculated using time-domain calculation methods, such as the arithmetic mean, harmonic mean, quadratic mean, weighted mean, median, geometric median, maximum, minimum, standard deviation (root mean square), area under the curve, peak-to-peak interval, Nonlinear Energy Operator, Shannon entropy, and/or Fisher entropy. In some embodiments, the physiological parameters may be calculated using frequency-domain calculation methods, such as Fast Fourier Transform, Hilbert Transform, Spectral entropy, high-pass filtering, low-pass filtering, band-pass filtering, and/or power of the frequency band.

The memory module 126 in the pulse generator 101 may include or communicate with the algorithm module 130 containing the algorithm. The algorithm may be used in a read-and-write mode during the learning phase. Once the learning phase is completed, the algorithm may be used in a read-only mode for the automatic operation phase. In the learning phase, the algorithm may collect sensor data, calculate the physiological parameters, correlate the patient-provided autonomic nervous system state, physiological state, and/or disease state with calculated physiological parameters, and correlate the autonomic nervous system state, physiological state, and/or disease state with present or patient-adjusted stimulation parameters. In the automatic operation phase, the algorithm may receive sensor data, calculate the physiological parameters, determine the autonomic nervous system state, physiological state, and/or disease state, and automatically set the stimulation parameters based on the correlation established during the learning phase.

In certain embodiments, the duration of the learning phase may be predetermined (e.g., 1 week, 1-2 weeks, 1-3 weeks, 1-4 weeks, 2-4 weeks, 2-5 weeks, 1-10 weeks, or longer) and may be set by the clinician, the device company representative, and/or other member of authorized personnel. In other embodiments, the duration of learning phase may be variable. For example, in some variations, the duration of the learning period may be determined using the preset confidence levels for the correlation weights stored in the pulse generator 101. In these variations, the learning phase may terminate when the correlation weights for certain autonomic nervous system states, physiological states, or disease states (e.g. "sympathetic activation", "during heavy meal", "after heavy meal", "flare"), have reached a specified or predetermined confidence level, for example, from about 80% to about 99%. In some variations, the patient and/or the clinician may terminate the learning phase irrespective of an elapsed time or current confidence level of the correlation weights, and/or may reset the pulse generator 101 with initial settings.

Once the autonomic nervous system states, physiological states, and/or disease states and corresponding stimulation parameters are established (e.g., once the learning phase is completed), the pulse generator 101 may automatically start, stop, or adjust the stimulation parameters based on the sensed measurements and calculated or determined autonomic nervous system state, physiological state, and/or disease state. In one example, when the pulse generator 101 receives sensor readings that indicate a food consumption state (e.g., "during light meal", "during heavy meal"), the pulse generator 101 may automatically increase a stimulation parameter (e.g., an amplitude) based on a corresponding value of the initial or patient-adjusted amplitude in the database for that food consumption state. In another example, when the pulse generator 101 receives sensor readings that indicate an "inflammatory response" disease state (e.g., "early inflammatory response", "late inflammatory response"), the pulse generator 101 may automatically decrease a stimulation parameter (e.g., an amplitude) based on a corresponding value of the initial or patient-adjusted amplitude in the database for "late inflammatory response" state when the disease state has changed from "early inflammatory response" to "late inflammatory response" state. In these examples, the patient need not manually operate the external programmer 104 in order to adjust the applied stimulation parameters. As a result, the therapy system 100 may be less cumbersome, time-consuming, and/or restrictive to operate than conventional systems.

In some variations, the pulse generator 101 may gradually adjust the stimulation parameters. For example, once the pulse generator 101 determines that a patient is in the disease state of "early inflammatory response", the pulse generator 101 may instruct the implantable signal delivery device 102 to apply a first stimulation signal. If the pulse generator 101 determines that the patient's disease state has changed to "late inflammatory response", the pulse generator 101 may instruct the implantable signal delivery device 102 to gradually apply a second (e.g. smaller amplitude) stimulation signal. In this variation, the second stimulation signal may be applied with a gradual ramp-down. In another example, once the pulse generator 101 determines that a patient is in a physiological state of "consuming a light meal", the pulse generator 101 may instruct the implantable signal delivery device 102 to apply a first stimulation signal. If the pulse generator 101 determines that the patient's physiological state has changed to "consuming a heavy meal", the pulse generator 101 may instruct the implantable signal delivery device 102 to gradually apply a second (e.g. larger amplitude) stimulation signal. In this variation, the second stimulation signal may be applied with a gradual ramp-up.

In some variations, instead of establishing individual stimulation parameters for each autonomic nervous system state, physiological state, and disease state, the system may provide gradually increasing or decreasing stimulation levels for a specific sequence of autonomic nervous system states, physiological states, and/or disease states. After the learning phase is completed, the pulse generator 101 may continue measuring and storing the current values of physiological parameters, determined autonomic nervous system state, physiological state, and/or disease state, and generated stimulation parameters, as described above. The pulse generator 101 may periodically (e.g., daily, weekly, biweekly, or the like) or continuously update (e.g., refine) the correlation weights based on these new measurements. In other embodiments, the process of further updating the correlation weights may be omitted.

In some embodiments, the pulse generator 101 may alert a patient and/or clinician, if a change is detected in one or more of the physiological parameters. For example, if the pulse generator 101 detects a large change (e.g., 10%, 20%, 30%, 40%, between 10%-20%, between 20%-30%) in one or more of the physiological parameters, the pulse generator 101 may output an alarm to the patient and/or the clinician indicating that an additional assessment is needed. In some variations, the patient and/or the clinician may decide when to reestablish the disease states based on changes in the patient's disease conditions, such as a progression of treated disease or appearance/disappearance of other diseases or medical conditions.

Algorithm

Figure 5:
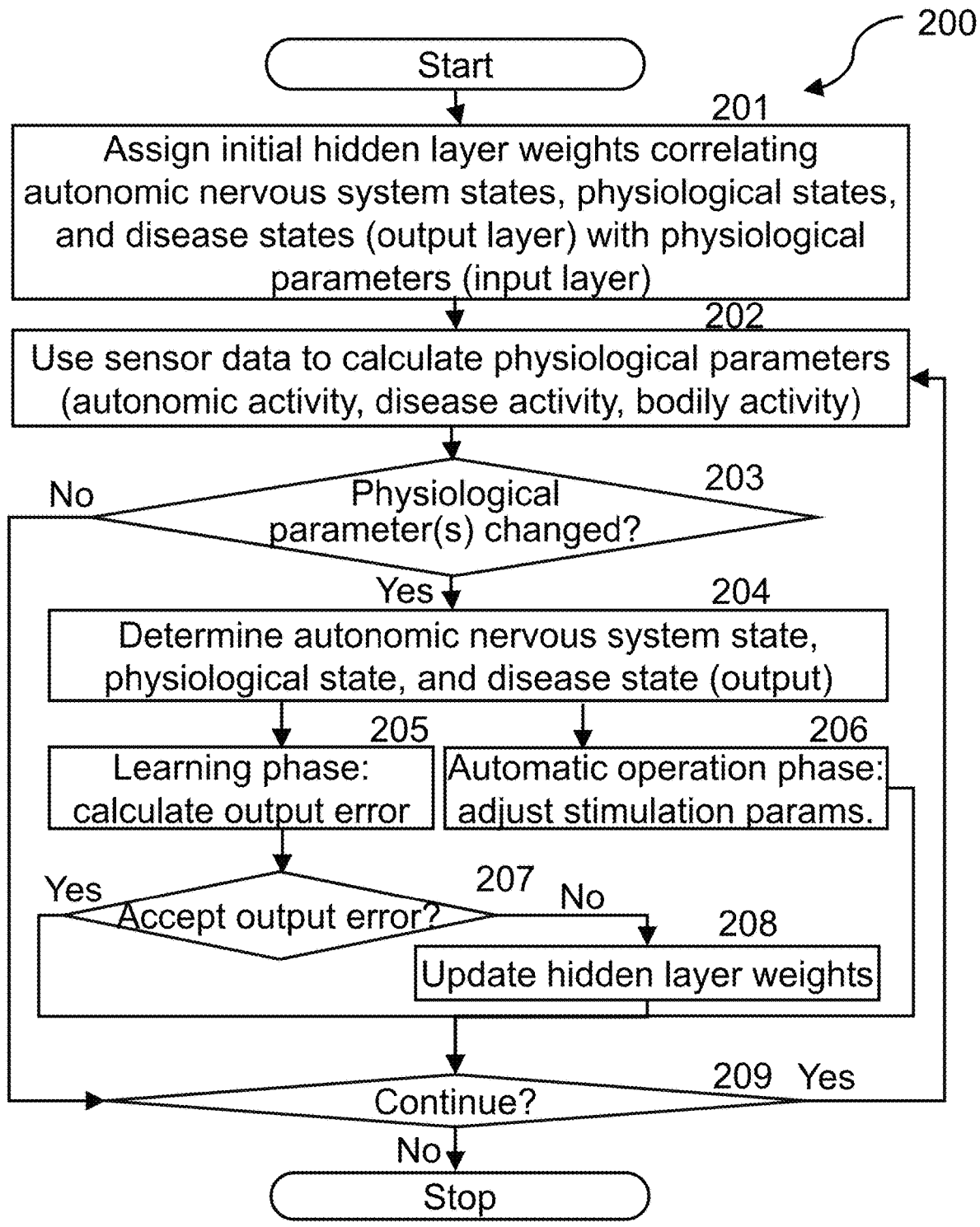
FIG. 5 is a flow diagram depicting a variation of a method for starting, stopping, and adjusting stimulation signals.

FIG. 5 is a flow diagram describing the steps of the learning and automatic phases of the algorithm 200 of the systems described here. The algorithm 200 depicted in FIG. 5 may allow the system to automatically adjust the stimulation signals delivered to a nerve (e.g., sacral nerve) based on the calculated physiological parameters (autonomic, disease, bodily activity) and on the autonomic nervous system states, physiological states, and/or disease states (e.g., patient-provided or determined). In the illustrated embodiment, the algorithm 200 uses a particular machine learning technique, the artificial neural network (ANN). Use of the algorithm depicted in FIG. 5 may reduce or eliminate the need for the patient and/or the clinician to interact with the external programmer 104 in the automatic operation phase.

Generally, the algorithm 200 depicted in FIG. 5 may comprise assigning initial hidden layer weights correlating the autonomic nervous system states, physiological states, and/or disease states (output layer) with physiological parameters (input layer), using the data from sensors (e.g. electrocardiographic or photoplethysmographic electrode and core body temperature sensor) to calculate physiological parameters (autonomic, disease activity, and bodily activity) (202), and determine whether one or more physiological parameters have changed above a delta change threshold (203). If the change in the physiological parameter is at or above a preset delta change threshold (e.g., 5-10% of the average), the algorithm 200 may further comprise calculating the autonomic nervous system state, physiological state, and/or disease state (output) (204). The next step in the algorithm 200 depicted in FIG. 5 depends on the current phase of the algorithm 200, i.e., whether the algorithm is in the learning phase or the automatic operation phase. During the learning phase, the algorithm 200 may calculate the output error between the determined autonomic nervous system state, physiological state, and/or disease state and the patient-provided autonomic nervous system state, physiological state, and/or disease state (205) and evaluate whether the output error is acceptable (207). In one embodiment, the evaluation is based on thresholding, with thresholds such as 5%, 10%, 15%, 20%, 10-20%, or 15%-20%. In different embodiments, other classification methods may be used, such as, for example, multiple linear regression, k nearest neighbor, linear discriminant analysis, feedforward neural network, convolutional neural network, random forest, logistic regression, or support vector machine. If the output error is above the acceptable level, the algorithm 200 may update the hidden layer weights based on the new correlations between the autonomic nervous system state, physiological state, and/or disease state classifications (output layer) with physiological parameters (input layer) (208). The ANN database of physiological parameters (input layer), the weights (hidden layer), and the autonomic nervous system states, physiological states, and/or disease states (output layer) may be updated as needed and stored in the memory module 126. During the automatic operation phase, instead of calculating the output error, the algorithm 200 may automatically adjusting the stimulation parameters, such an amplitude, a frequency, an electrode contact arrangement, and/or other suitable stimulation parameters, (206) based on determining a new autonomic nervous system state, physiological state, and/or disease state (204). In some variations, the algorithm 200 may stop when the correlation weights reach or exceed the preset confidence level (209). In some instances, the algorithm 200 may also be stopped and/or restarted manually by a clinician based on changes in patient's disease conditions.

In some embodiments, the system may provide (e.g., via the implantable pulse generator, via a computer) a warning signal to the patient indicating that the ANN update has been performed and/or that a clinician should perform a checkup. The clinician may then determine whether the implantable signal delivery device 102 (FIG. 1) requires any physical adjustment. If so, the clinician may readjust the implantable signal delivery device 102 and restart the algorithm at the step of assigning initial hidden layer weights (201).

In some variations, the algorithm described here may be implemented without a clear distinction between the learning phase and the automatic operation phase. Instead, both phases may be executed simultaneously. For example, in these variations, the method may comprise tracking the physiological parameters for a sliding period of time (e.g., 1 week, 2 weeks, 1-2 weeks, or more), while continuously or intermittently updating the correlation weights between physiological parameters and autonomic nervous system states, physiological states, and/or disease states (205) and the patient-adjusted stimulation parameters (206). For example, if the patient manually overrides the preset stimulation parameters for a particular autonomic nervous system state, physiological state, and/or disease state, the algorithm may update the correlation weight with the patient selection. The weight adjustment may depend on the frequency with which each stimulation parameter is selected and/or the duration of use for each stimulation parameter. In other embodiments, the weights may be adjusted in other ways. For example, in some variations, the most recent patient selection may receive the highest weight.

Figure 6:
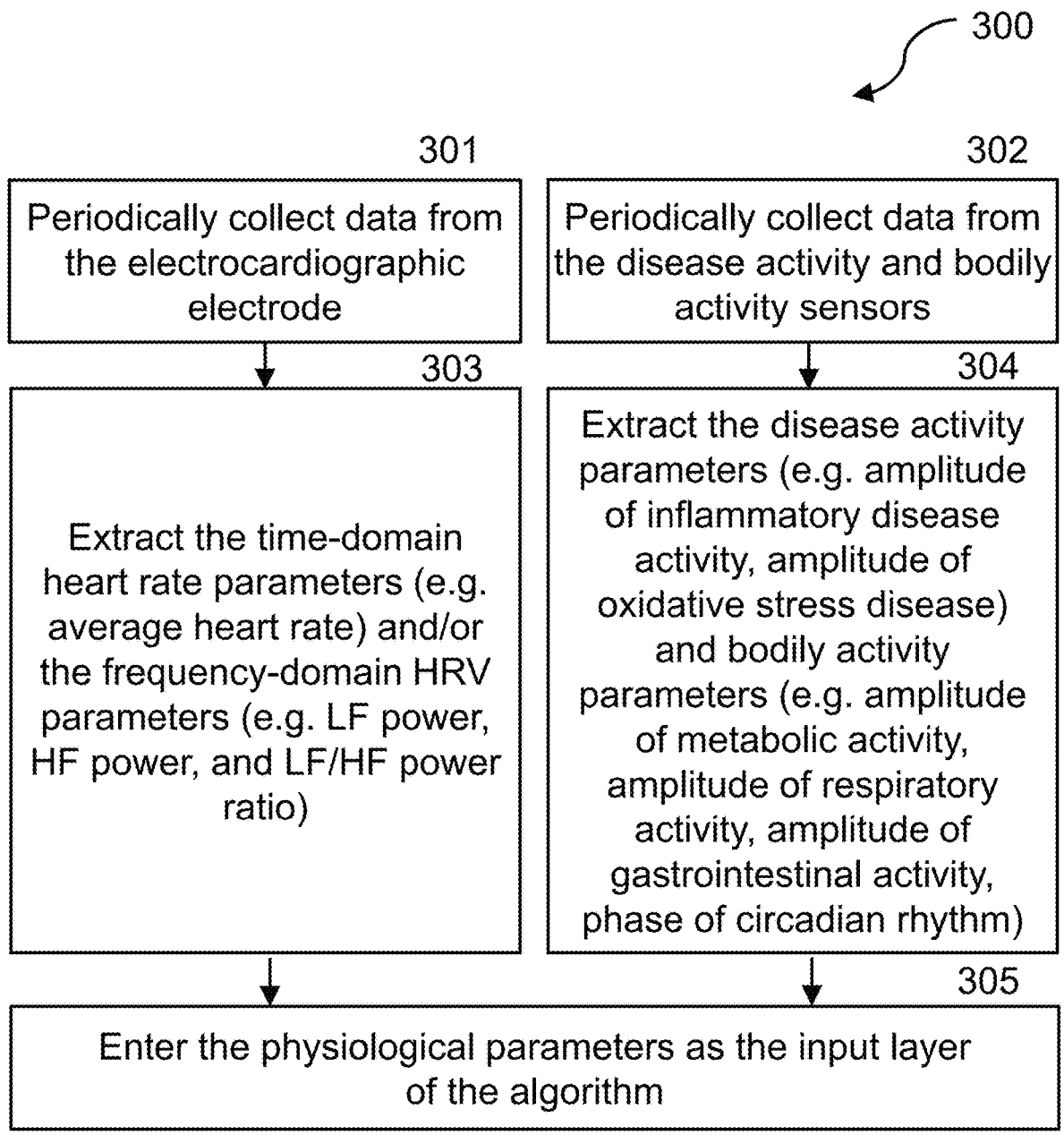
FIG. 6 is a flow diagram depicting an exemplary process for tracking incoming data for physiological parameters.

FIG. 6 is a flow diagram illustrating a method for measuring or receiving and processing autonomic nervous system data from a first sensor (e.g., an autonomic nervous system sensor), and a second sensor (e.g., a disease activity sensor and/or a bodily activity sensor) or from a second sensor (e.g., a disease activity sensor) and a third sensor (e.g., a bodily activity sensor). In particular, FIG. 6 depicts a flow diagram illustrating a method for collecting data for the physiological parameters (300) based on the time-domain and frequency-domain heart rate parameters, disease activity parameters, and bodily activity parameters. As shown there, the method (300) may comprise collecting data, e.g., periodically, from a cardiac sensor (e.g., an electrocardiographic or photoplethysmographic electrode) (301), extracting the heart rate parameters including, for example, time-domain heart rate parameters such as average heart rate, HRV, HRT onset, and HRT slope and/or the frequency-domain HRV parameters such as LF power, HF power, and the LF/HF power ratio (303) from the collected data, and using the extracted heart rate parameters to deliver, control, and/or adjust stimulation delivery (e.g., by entering the heart rate parameters as the input layer of the algorithm) (305).

Additionally or alternatively, the method (300) may comprise collecting data, e.g., continuously or intermittently, from one or more disease activity and/or bodily activity sensors (302). The disease activity sensor may be an inflammatory disease activity sensor and/or oxidative stress disease activity sensor. The method (300) may further comprise extracting the disease activity parameters (e.g. amplitude of inflammatory disease activity, amplitude of oxidative stress disease activity) and bodily activity parameters (e.g. amplitude of metabolic activity, amplitude of respiratory activity, amplitude of gastrointestinal activity, awake or asleep phase of circadian rhythm) (304) from the collected data, and using the extracted parameters to deliver, control, and/or adjust stimulation delivery (e.g., by entering the disease activity parameters as the input layer of the algorithm) (305).

Accordingly, the method (300) may comprise collecting data from a cardiac sensor (e.g., an electrocardiographic or photoplethysmographic electrode), a disease activity sensor (e.g. an inflammatory disease activity sensor or an oxidative stress disease activity sensor) and a bodily activity sensor (e.g., a metabolic activity sensor, a respiratory activity sensor, a gastrointestinal activity sensor or a circadian rhythm sensor), extracting the time domain heart rate parameters and/or the frequency-domain HRV values from the data from the cardiac sensor, extracting the disease activity parameters from the data from the disease activity sensor, extracting the bodily activity parameters from the data from the bodily activity sensor, and utilizing one or more of the extracted parameters to determine an autonomic nervous system state, physiological state, and/or disease state and ultimately deliver, control, and/or adjust stimulation signal delivery.

In some instances, the method may comprise collecting data from a disease activity sensor (e.g. an inflammatory disease activity sensor or an oxidative stress disease activity sensor), extracting the disease activity parameters from the data from the disease activity sensor, and utilizing the extracted parameters to determine an autonomic nervous system state, physiological state, or disease state, and ultimately deliver, control, and/or adjust stimulation signal delivery. In other variations, the method may comprise collecting data from a disease activity sensor and a bodily activity sensor, extracting the disease activity parameters from the data from the disease activity sensor, extracting the bodily activity parameters from the data from the bodily activity sensor, utilizing the disease activity parameters and the bodily activity parameters to determine an autonomic nervous system state, physiological state, and/or disease state and ultimately deliver, control, and/or adjust stimulation signal delivery. In some of these variations, the disease activity sensor and the bodily activity sensor may be the same sensor, and may be referred to herein as an activity sensor (e.g., a single core body temperature sensor). In yet other variations, the method may comprise collecting data from a disease activity sensor and an autonomic activity sensor, extracting the disease activity parameters from the data from the disease activity sensor, extracting the autonomic activity parameters from the data from autonomic activity sensor, utilizing the disease activity parameters and the autonomic activity parameters to determine an autonomic nervous system state, physiological state, and/or disease state and ultimately deliver, control, and/or adjust stimulation signal delivery. Accordingly, the methods described here need not utilize parameters from all three parameter groups to determine autonomic nervous system state, physiological state, and/or disease state and ultimately deliver, control and/or adjust stimulation signal delivery.

FIG. 7 illustrates the use of frequency-domain HRV parameters calculated from electrocardiographic data, and particularly the LF/HF power ratio. FIG. 7 depicts the change in the LF/HF power ratio over time during varying autonomic nervous system states. In particular, the upper plot illustrates how the LF/HF power ratio increases during food consumption-induced parasympathetic activation (401), while the lower plot illustrates how the LF/HF power ratio decreases during exercise-induced sympathetic activation (402). The LF/HF power ratio may increase during parasympathetic activation, which occurs immediately after initiation of food consumption and may subside to a low level soon after completing food consumption. Additionally, the LF/HF power ratio may decrease during sympathetic activation induced by exercise. The LF/HF power ratio, therefore, has a good predictive value for at least distinguishing the autonomic nervous system state "parasympathetic activation" from "sympathetic activation". The correlation weight between the physiological parameter "LF/HF power ratio" and the autonomic nervous system states "parasympathetic activation" and "sympathetic activation" will gradually become high (with either positive or negative weight for these two states) during the learning phase, illustrating how the correlation weights for HRV parameters may be adjusted during the learning phase of the algorithm operation.

FIG. 8 illustrates an example of bodily activity data, and specifically, metabolic activity data, and disease activity data, collected continuously with a core body temperature sensor (in this example, the bodily activity data and the disease activity data are collected using the same sensor). The plots in FIG. 8 depict changes in metabolic activity and disease activity as observed in two patients during several autonomic nervous system states, physiological states, and disease states. The upper plot illustrates changes in core body temperature (501) on two consecutive days during two physiological states: dinner (DN) and sleep, and two disease states: early inflammatory response (EIR) and late inflammatory response (LIR) to a vaccination. As can be seen in the upper plot, the patient's core body temperature increases slightly after dinner and decreases considerably (e.g., 1.5-2 degrees Celsius or more) during sleep. During EIR, the patient's core body temperature increases considerably and for a prolonged period of time (about 6 hours). This suggests that a prolonged increase (e.g., over 6 hours or more) in core body temperature, or a larger percentage of time with elevated core body temperature, may be indicative of inflammatory disease and that prolonged elevated core body temperature may thus serve as a parameter that informs a disease state. During LIR, the patient's core body temperature is not significantly increased, but shows large fluctuations. This suggests that amplitude, or changes in amplitude, of core body temperature may be indicative of inflammatory disease activity and that amplitude of core body temperature may thus serve as a parameter that informs a disease state.

The lower plot in FIG. 8 illustrates changes in core body temperature (502) on three consecutive days during several physiological states: dinner (DN), sleep, breakfast (BF), and lunch (LN). Similarly to the upper plot, the core body temperature increases after each meal (DN, BF, or LN) and decreases considerably during sleep. Therefore, the amplitude of core body temperature, and in particular, the shorter duration average (e.g., mean amplitude over 1 hour) has a good predictive value for detecting the physiological states related to meal consumption, which may be reflected in a high correlation weight between this physiological parameter and the physiological states of DN, BF, and LN. In contrast, a longer duration average (e.g., a six hour mean of amplitude) has a good predictive value for detecting inflammatory disease activity. This illustrates how the correlation weights for different physiological parameters (e.g., disease activity parameters, bodily activity parameters) collected from the same sensor (e.g. core body temperature sensor) may be assigned and adjusted for various autonomic nervous system states, physiological states, and/or disease states during the learning phase of the algorithm operation. While described in this example in relation to core body temperature in particular, it should be appreciated that the bodily activity parameters and disease activity parameters described above are also useful in determining autonomic nervous system states, physiological states, and/or disease states from disease activity data and bodily activity data collected from other types of sensors.

Figure 9:
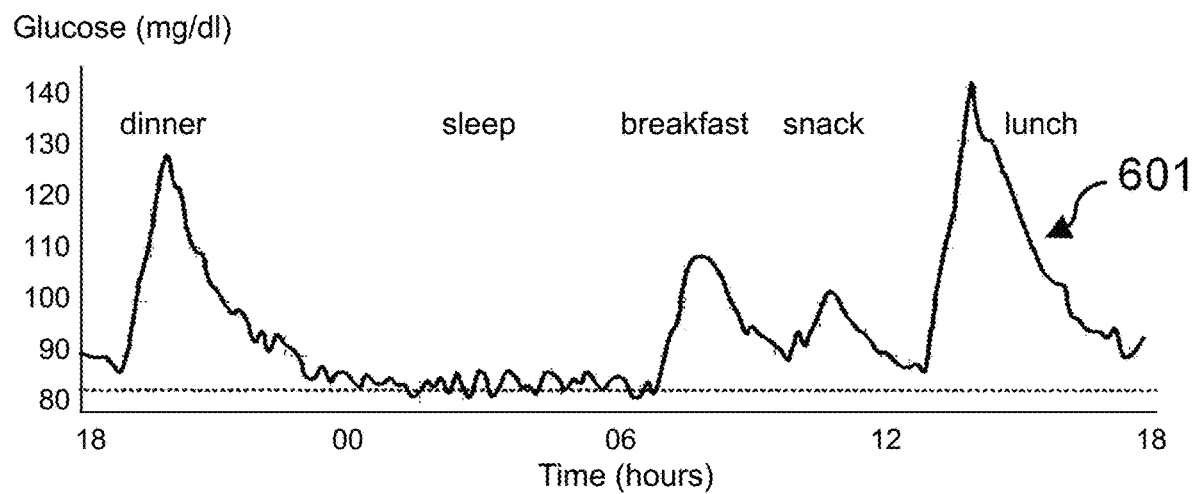
FIG. 9 graphically illustrates changes in metabolic activity during several physiological states, collected continuously with an electrochemical glucose sensor.

FIG. 9 illustrates changes in bodily activity, and in particular, metabolic activity, during several physiological states, collected continuously with an electrochemical glucose sensor. As can be seen in the plot in FIG. 9, the patient's glucose increases considerably after dinner and lunch, increases slightly after breakfast and snack, and decreases considerably (e.g., by at least about 20-30%) during sleep (601). As compared with FIG. 8, this example illustrates how a physiological parameter, and in particular, a bodily activity parameter (e.g. amplitude of metabolic activity) can be extracted from data from different sensors (e.g. a core body temperature sensor versus a glucose sensor).

FIG. 10 illustrates the learning phase of the algorithm, in which the ANN is being trained using backpropagation. The experiment was performed in a non-diseased subject, fitted with wrist-worn electrocardiographic electrode for calculating the autonomic HRV parameters (e.g. LF power, HF power, LF/HF ratio) and with a core body temperature sensor located in the large colon for calculating the disease activity parameters (e.g. amplitude of inflammatory disease activity). The subject provided information about various autonomic nervous system states, physiological states, and/or disease states (701), such as sympathetic activation, flare, physical exercise, during light meal, during heavy meal, after heavy meal. The physiological states for deep sleep and REM sleep were determined automatically from circadian rhythm phases using the data from the wrist-worn electrocardiographic or photoplethysmographic electrode.

As shown there, the ANN may be structured in three layers (input, hidden, output). During the learning phase, the ANN may correlate various patient-provided autonomic nervous system states, physiological states, or disease states (701) with various physiological parameters, which may serve as the input layer nodes (702). Correlation weights of the hidden layer nodes (703) may be assigned by correlating the input layer nodes (physiological parameters) with the output layer node (704) containing the autonomic nervous system states, physiological states, and disease states determined by the ANN. Then, the output error between the weights for the ANN-determined autonomic nervous system states, physiological states, and disease states (704) and for the patient-provided autonomic nervous system state, physiological state, or disease state (701) may be calculated. For better visualization, the values for the input layer notes are represented as low, medium, and high and the nodes are shaded accordingly (low—light shade, medium—medium shade, high—dark shade).

As can be seen in FIG. 10, in some instances, the values for autonomic HRV parameters (e.g., LF power, HF power, LF/HF ratio) and disease activity parameters (e.g., inflammatory disease activity amplitude (IDA amp.), amplitude of metabolic activity (MA amp)) may be the same or similar during two or more autonomic nervous system states, physiological states, and/or disease states such that it may be difficult to accurately determine the autonomic nervous system state, physiological state, and/or disease state based on the autonomic HRV parameters or disease activity parameters without additional parameters. For example, the LF power, HF power, and LF/HF ratio may be high, low, and high respectively, during several physiological states, e.g., "during heavy meal" and "REM sleep." Similarly, in some instances, the values for one or more of the disease activity parameters (e.g., IDA amp., MA amp.) may also be the same or similar during two or more autonomic nervous system states, physiological states, or disease states. For example, the MA amp. may be elevated to medium during a disease state of "flare" as well as during two physiological states "during light meal" and "after heavy meal". Thus, in some instances, it may also be difficult to accurately determine the autonomic nervous system state, physiological state, or disease state of a patient based on the disease activity parameters alone. Thus, utilization of several physiological parameters, including one or more of the autonomic nervous system parameters (e.g., LF power, HF power, LF/HF ratio), disease activity parameters (e.g., IDA amp.), and bodily activity parameters (e.g., sleep phase of the circadian rhythm (CR sleep) or awake phase of the circadian rhythm) may provide a more accurate determination of an autonomic nervous system state, physiological state, and/or disease state of a patient. By more accurately determining the autonomic nervous system states, physiological states, and/or disease states (and especially for distinguishing the disease states from particular physiological states) and adjusting the stimulation parameters accordingly, the devices, systems, and methods described here may better control a patient's disease and/or symptoms of the disease, and may reduce the frequency and severity of unwanted side effects.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/or advantages. These also include embodiments in which the components and/or steps are arranged and/or ordered differently.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element proceeded by an "a" or an "an" does not, without further constraints, preclude the existence of additional elements of the identical type.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. A method for delivering a stimulation signal to a nerve of a patient comprising:
   receiving inflammatory disease activity data from an inflammatory disease activity sensor;
   calculating a time-dependent inflammatory disease activity parameter based on at least a portion of the inflammatory disease activity data;
   determining an inflammatory disease state of the patient based on the time-dependent inflammatory disease activity parameter, wherein the inflammatory disease state is early inflammatory response, flare of inflammatory disease activity, no flare in inflammatory disease activity, or late inflammatory response;
   adjusting a nerve stimulation parameter of a stimulation signal based on the determined inflammatory disease state; and
   applying an adjusted stimulation signal comprising the adjusted nerve stimulation parameter to the nerve of the patient.

2. The method of claim 1, wherein the nerve is the sacral nerve.

3. The method of claim 1, wherein calculating the time-dependent inflammatory disease activity parameter comprises calculating one or more of: an average of inflammatory disease activity data and a percentage of time with elevated inflammatory disease activity.

4. The method of claim 1, wherein the inflammatory disease activity sensor is an implanted core body temperature sensor and the inflammatory disease activity data is core body temperature data.

5. The method of claim 4, wherein calculating the time-dependent inflammatory disease activity parameter comprises calculating an average of core body temperature or a percentage of time with elevated core body temperature.

6. The method of claim 1, further comprising receiving electrocardiographic or photoplethysmographic data from a cardiac sensor.

7. The method of claim 6, further comprising calculating a heart rate parameter from the electrocardiographic or photoplethysmographic data and determining an autonomic nervous system state based on the heart rate parameter.

8. The method of claim 7, wherein the nerve stimulation parameter is adjusted based on the inflammatory disease state and the autonomic nervous system state.

9. The method of claim 7, wherein the heart rate parameter comprises a frequency-domain parameter.

10. The method of claim 1, wherein the time-dependent inflammatory disease activity parameter is calculated over a period of time of about 1 hour to about 12 hours.

11. The method of claim 1, wherein the inflammatory disease state is flare of inflammatory disease activity, and wherein in the inflammatory disease state of flare, inflammatory disease activity in an inflammatory, auto-immune, or metabolic disease is increased.

12. The method of claim 1, further comprising receiving bodily activity data from a bodily activity sensor.

13. The method of claim 12, wherein the inflammatory disease activity sensor and the bodily activity sensor are the same sensor.

14. The method of claim 13, wherein the inflammatory disease activity sensor and the bodily activity sensor are a single implanted core body temperature sensor.

15. The method of claim 12, wherein the inflammatory disease state is determined based on the time-dependent inflammatory disease activity parameter and the bodily activity data.

16. The method of claim 15 further comprising calculating a bodily activity parameter from the bodily activity data, wherein the inflammatory disease state is determined-based on the time-dependent inflammatory disease activity parameter and the bodily activity parameter.

17. The method of claim 16, wherein the bodily activity parameter comprises a respiratory activity parameter, a metabolic activity parameter, a gastrointestinal activity parameter, or a circadian rhythm parameter.

18. The method of claim 1, wherein the adjusted nerve stimulation parameter comprises one or more of amplitude, frequency, pulse width, burst interval, and elapsed duration.

19. The method of claim 1 further comprising delivering a screening stimulation signal to the nerve using a temporary signal delivery device.

20. The method of claim 1, wherein the adjusted stimulation signal is delivered using an implantable signal delivery device or a temporary signal delivery device.

21. The method of claim 1, wherein the adjusted stimulation signal is discontinuous.

22. The method of claim 1, wherein the nerve is the sacral nerve and wherein application of the adjusted stimulation signal to the sacral nerve suppresses the production of pro-inflammatory cytokines, increases the production of anti-inflammatory cytokines, and/or reduces the sympathetic tone in a patient that has a chronic gastrointestinal disorder, a chronic auto-immune disease, or a metabolic disorder.

23. A method for delivering a stimulation signal to a sacral nerve of a patient comprising:
   receiving electrocardiographic or photoplethysmographic data from a cardiac sensor;
   receiving temperature data from an implanted core body temperature sensor;
   determining a heart rate parameter from the electrocardiographic or photoplethysmographic data;
   calculating a time-dependent inflammatory disease activity parameter and a bodily activity parameter based on at least a portion of the temperature data;
   determining an autonomic nervous system state from the heart rate parameter, a physiological state from the bodily activity parameter and an inflammatory disease state from the time-dependent inflammatory disease activity parameter, wherein the inflammatory disease state is early inflammatory response, flare of inflammatory disease activity, no flare in inflammatory disease activity, or late inflammatory response;
   adjusting a nerve stimulation parameter of a stimulation signal based on the determined inflammatory disease state; and
   applying an adjusted stimulation signal comprising the adjusted nerve stimulation parameter to the sacral nerve of the patient.

24. The method of claim 23, wherein the nerve stimulation parameter is adjusted based on the determined inflammatory disease state and the determined autonomic nervous system state.

25. The method of claim 23, wherein the nerve stimulation parameter is adjusted based on the determined inflammatory disease state and the determined physiological state.

26. The method of claim 23, where in the nerve stimulation parameter is adjusted based on the determined inflammatory disease state, the determined physiological state, and the determined autonomic nervous system state.

27. The method of claim 23, wherein the time-dependent inflammatory disease activity parameter is calculated over a period of time of about 1 hour to about 12 hours.

28. The method of claim 23, wherein calculating the time-dependent inflammatory disease activity parameter comprises calculating an average of the temperature data over a period of time or a percentage of time with elevated core body temperature.

29. The method of claim 23, wherein the heart rate parameter comprises a frequency-domain parameter.

30. The method of claim 29, wherein the frequency-domain parameter comprises a power of a low frequency (LF) band, a power of a high frequency (HF) band, or an LF/HF power ratio.

31. The method of claim 23, wherein the inflammatory disease state is flare of inflammatory disease activity, and wherein in the inflammatory disease state of flare, inflammatory disease activity in an inflammatory, auto-immune, or metabolic disease is increased.

\* \* \* \* \*